(12) United States Patent
Kinzler et al.

(10) Patent No.: US 8,541,559 B2
(45) Date of Patent: Sep. 24, 2013

(54) PROCESS FOR PRODUCING AGGREGATED OLIGONUCLEOTIDES

(75) Inventors: Matthias Kinzler, Zurich (CH); Karl Proba, Zurich (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 733 days.

(21) Appl. No.: 12/304,620

(22) PCT Filed: Jun. 12, 2007

(86) PCT No.: PCT/EP2007/005188
§ 371 (c)(1),
(2), (4) Date: Nov. 25, 2009

(87) PCT Pub. No.: WO2007/144150
PCT Pub. Date: Dec. 21, 2007

(65) Prior Publication Data
US 2010/0273237 A1    Oct. 28, 2010

Related U.S. Application Data

(60) Provisional application No. 60/812,592, filed on Jun. 12, 2006.

(51) Int. Cl.
*C07H 21/04* (2006.01)
(52) U.S. Cl.
USPC .......................................................... 536/23.1
(58) Field of Classification Search
None
See application file for complete search history.

(56) References Cited

U.S. PATENT DOCUMENTS

| | | |
|---|---|---|
| 2003/0099668 A1 | 5/2003 | Bachmann et al. |
| 2004/0005338 A1 | 1/2004 | Bachmann et al. |
| 2006/0204475 A1 | 9/2006 | Bachmann et al. |
| 2006/0210588 A1 | 9/2006 | Bachmann et al. |
| 2006/0251623 A1 | 11/2006 | Bachmann et al. |
| 2006/0251677 A1 | 11/2006 | Bachmann et al. |
| 2008/0292652 A1 | 11/2008 | Bachmann et al. |

FOREIGN PATENT DOCUMENTS

| | | |
|---|---|---|
| WO | WO 03/024480 A2 | 3/2003 |
| WO | WO 03/024481 A2 | 3/2003 |
| WO | WO 2004/000351 | * 12/2003 |
| WO | WO 2004/000351 A1 | 12/2003 |
| WO | WO 2004/084940 A1 | 10/2004 |
| WO | WO 2005/117963 A1 | 12/2005 |
| WO | WO 2007/039552 A1 | 4/2007 |

OTHER PUBLICATIONS

Biyani et al., Gene, 2005, 364:130-138.*
Marsh et al., Nucleic Acids Research, 1995, 23(4):696-700.*
Costa, L.T., et al., "Structural Studies of Oligonucleotides Containing G-quadruplex Motifs Using AFM," *Biochem. Biophys. Res. Commun.* 313:1065-1072, Elsevier Inc. (2004).
Kerkmann, M., et al., "Spontaneous Formation of Nucleic Acid-based Nanoparticles is Responsible for High Interferon-α Induction by CpG-A in Plasmacytoid Dendritic Cells," *J. Biol. Chem.* 280:8086-8093, The American Society for Biochemistry and Molecular Biology, Inc. (2005).
Lu, M., et al., "Structure and Stability of Sodium and Potassium Complexes of $dT_4G_4$ and $dT_4G_4T$," *Biochemistry* 31:2455-2459, American Chemical Society (1992).
Storni, T., et al., "Nonmethylated CG Motifs Packaged into Virus-Like Particles Induce Protective Cytotoxic T Cell Responses in the Absence of Systemic Side Effects." *J. Immunol.* 172:1777-1785, The American Association of Immunologists, Inc. (2004).

* cited by examiner

*Primary Examiner* — Zachariah Lucas
*Assistant Examiner* — Nicole Kinsey White
(74) *Attorney, Agent, or Firm* — Sterne, Kessler, Goldstein & Fox PLLC

(57) ABSTRACT

The invention provides processes for the producing compositions comprising (i) a virus-like particle, wherein said virus-like particle is a virus-like particle of an RNA bacteriophage, and (ii) an oligonucleotide, wherein said oligonucleotide is packaged into said virus-like particle. The invention further provides processes for producing nucleotide compositions comprising oligonucleotides suitable to be used in the processes mentioned before. The invention further provides nucleotide compositions obtainable by the processes of the invention and uses thereof. The invention further provides compositions comprising (i) a virus-like particle, wherein said virus-like particle is a virus-like particle of an RNA bacteriophage, and (ii) an oligonucleotide, wherein said oligonucleotide is packaged into said virus-like particle, wherein said compositions are obtainable by the processes of the invention and wherein said compositions preferably comprises a purity of at least 98%, most preferably of at least 99%.

20 Claims, 6 Drawing Sheets

PROCESS FOR PRODUCING AGGREGATED OLIGONUCLEOTIDES

CROSS-REFERENCE TO RELATED APPLICATIONS

This application is the U.S. National Phase of International Application PCT/EP2007/005188, international filing date of Jun. 12, 2007, and claims the benefit of the filing date of International Application PCT/EP06/69734, filed on Dec. 14, 2006, and the filing date of U.S. Provisional Application 60/812,592, filed Jun. 12, 2006, all of which are herein incorporated by reference.

FIELD OF THE INVENTION

The invention provides processes for the producing compositions comprising (i) a virus-like particle, wherein said virus-like particle is a virus-like particle of an RNA bacteriophage, and (ii) an oligonucleotide, wherein said oligonucleotide is packaged into said virus-like particle. The invention further provides processes for producing nucleotide compositions comprising oligonucleotides suitable to be used in the processes mentioned before. The invention further provides nucleotide compositions obtainable by the processes of the invention and uses thereof. The invention further provides compositions comprising (i) a virus-like particle, wherein said virus-like particle is a virus-like particle of an RNA bacteriophage, and (ii) an oligonucleotide, wherein said oligonucleotide is packaged into said virus-like particle, wherein said compositions are obtainable by the processes of the invention and wherein said compositions preferably comprises a purity of at least 98%, most preferably of at least 99%.

RELATED ART

Virus-like particles of RNA bacteriophages packaged with oligonucleotides are potent stimulators of the immune system (WO2003/024481A2) and are widely used in modern vaccination treatments. Processes for producing compositions comprising (i) a virus-like particle, wherein said virus-like particle is a virus-like particle of an RNA bacteriophage, and (ii) an oligonucleotide, wherein said oligonucleotide is packaged into said virus-like particle have been described, for example, in WO2003/024481A2, WO2004/000351A1, WO2004/084940A1 and WO2004/007538A2. Processes which are based on the disassembly of a recombinant virus-like particle, the purification of the coat protein and the reassembly of said coat protein in the presence of nucleic acid are most commonly used. Efficient and scalable processes for the production of recombinant virus-like particles of RNA bacteriophages are disclosed in WO2005/117963A1. Processes for the large scale purification of endotoxin free, intact virus-like particles are disclosed in WO2007/039552A1. Processes for the preparation of coat protein from recombinantly produced virus like particles ("disassembly") are disclosed, inter alia, in WO2003/024481A2, and in the examples section of the present application. The processes for the assembly of coat protein in the presence of nucleic acid ("reassembly") disclosed in the prior are not optimized with respect to efficiency, scalability and purity of the assembled product. In particular, the prior art does not teach that the efficiency of the "reassembly" process, can be dramatically improved by using aggregated oligonucleotide comprising a certain particle size (herein characterized by the relative peak start time, see below). This application provides a "reassembly" process with dramatically enhanced efficiency leading to a packaging product of very high purity. Typically and preferably the "reassembly" process disclosed herein comprises a protein yield and an oligonucleotide yield of at least about 75% and results in a product (composition comprising a virus-like particle packaged with oligonucleotide) which typically and preferably is at least 99% pure.

SUMMARY OF THE INVENTION

The invention relates to a process for producing a nucleotide composition comprising (i) a virus-like particle, wherein said virus-like particle is a virus-like particle of an RNA bacteriophage, and (ii) an oligonucleotide, wherein said oligonucleotide is packaged into said virus-like particle. During said process said virus-like particle is formed by self assembly of coat protein of said RNA bacteriophage in the presence of an oligonucleotide. It has surprisingly been found that the efficiency of process can be significantly improved when the self assembly of the coat protein is performed in the presence of aggregated oligonucleotide. Generally, oligonucleotides comprising at least one poly G stretch are capable of aggregation. The aggregation state of an oligonucleotide can be characterized by the relative peak start time in size exclusion HPLC using the capsid of said RNA bacteriophage as standard. Oligonucleotide comprising a relative peak start time of 50 to 110%, preferably of 80 to 95%, has been found to be optimal. This corresponds to oligonucleotide aggregates comprising an apparent molecular weight which is in the range of the apparent molecular weight of the capsid of said RNA bacteriophage or slightly below. It has been found that oligonucleotide comprising the desired relative peak start time can be obtained by subjecting said oligonucleotide to an aggregation process.

Thus, a first aspect of the invention is a process for producing a nucleotide composition comprising an oligonucleotide, wherein preferably said oligonucleotide comprises a relative peak start time of 50 to 110%, said process comprising the steps of: (a) providing an oligonucleotide in a solution II, wherein said oligonucleotide at least one poly G stretch; and wherein said solution II comprises a pH of 5 to 8; and wherein said solution II comprises a cation, wherein preferably the concentration of said cation in said solution II is at least 20 mM, wherein said cation is preferably selected from the group consisting of $Na^+$, $K^+$, $NH_4^+$, $Li^+$, $Ca^{2+}$, and $Mg^{2+}$; (b) adjusting the temperature of solution II to temperature III wherein said temperature III is 50 to 99° C.; and (c) incubating said oligonucleotide in solution II at temperature III, wherein said incubating is performed until said oligonucleotide comprises a relative peak start time of 50 to 110%; and (d) adjusting the temperature of solution II to temperature IV, wherein said temperature IV is below 50° C.; wherein said steps are preferably performed in the given order.

The self assembly of said coat protein is most efficient when the oligonucleotide preparation comprises aggregates comprising the optimal particle size and a narrow size distribution. Further surprisingly it has been found that the aggregation state of the oligonucleotide can be controlled more efficiently and that oligonucleotide preparations with a more narrow size distribution are obtained, when the oligonucleotide is subjected to a disaggregation step prior to the aggregation step. Said process may comprise any one of the features and embodiments described herein in any combination.

Thus, a second aspect of the invention is a process for producing a nucleotide composition comprising an oligonucleotide, wherein preferably said oligonucleotide comprises a relative peak start time of 50 to 110%, said process comprising the steps of: (a) providing an oligonucleotide in solution I, wherein said oligonucleotide at least one poly G stretch; and wherein said solution I comprises an alkaline pH; (b) disaggregating said oligonucleotide, wherein said disaggregating comprises the steps of: (i) adjusting the temperature of solution I to temperature I, wherein said temperature I is 4 to 70° C.; (ii) incubating said oligonucleotide in said solution I at said temperature I, wherein said incubating is performed until said oligonucleotide comprises a relative peak start time above 110%; and (iii) adjusting the temperature of said solution I to temperature II, wherein said temperature II is 0 to 70° C.; (c) adjusting the pH of said solution I to pH 5 to 8; and (d) aggregating said oligonucleotide, wherein said aggregating comprises the steps of: (i) providing said oligonucleotide in solution II, wherein said solution II comprises pH 5 to 8 and a cation, wherein preferably the concentration of said cation in said solution II is at least 20 mM, and wherein preferably said cation is selected from the group consisting of $Na^+$, $K^+$, $NH_4^+$, $Li^+$, $Ca^{2+}$, and $Mg^{2+}$; (ii) adjusting the temperature of solution II to temperature III, wherein said temperature III is 50 to 99° C.; (iii) incubating said oligonucleotide in solution II at temperature III, wherein said incubating is performed until said oligonucleotide comprises a relative peak start time of 50 to 110%; and (iv) adjusting the temperature of solution II to temperature IV, wherein said temperature IV is below 50° C.; wherein said steps are preferably performed in the given order. Said process may comprise any one of the features and embodiments described herein in any combination.

A third aspect of the invention is a nucleotide composition comprising an oligonucleotide, wherein said nucleotide composition is obtainable by any one of the processes described above, wherein preferably said oligonucleotide comprises a relative peak start time of 50 to 110%. Said nucleotide composition may comprise any one of the features and embodiments described herein in any combination.

A fourth aspect of the invention is a process for producing a composition comprising (i) a virus-like particle, wherein said virus-like particle is a virus-like particle of an RNA bacteriophage, and (ii) an oligonucleotide, wherein said oligonucleotide is packaged into said virus-like particle, said process comprising the steps of: (a) providing coat protein of said RNA bacteriophage; (b) providing a nucleotide composition comprising an oligonucleotide, wherein said nucleotide composition is a nucleotide composition obtainable by any one of the processes of the first and the second aspect of the invention; (c) generating a mixture, wherein said mixture comprises: (i) said coat protein; (ii) an agent capable of preventing the self-assembly of said coat protein; (iii) said oligonucleotide; (d) removing said agent from said mixture; and (e) allowing said coat protein to self assemble into a virus-like particle. Said process may comprise any one of the features and embodiments described herein in any combination.

A fifth aspect of the invention is a process for producing a composition comprising (i) a virus-like particle, wherein said virus-like particle is a virus-like particle of an RNA bacteriophage, and (ii) an oligonucleotide, wherein said oligonucleotide is packaged into said virus-like particle, said process comprising the steps of: (a) providing coat protein of said RNA bacteriophage; (b) providing an oligonucleotide, (i) wherein said oligonucleotide at least one poly G stretch; and (ii) wherein said oligonucleotide comprise a relative peak start time of 50 to 110%; (c) generating a mixture, wherein said mixture comprises: (i) said coat protein; (ii) an agent capable of preventing the self-assembly of said coat protein; (iii) said oligonucleotide; (d) removing said agent from said mixture; and (e) allowing said coat protein to self assemble into a virus-like particle. Said process may comprise any one of the features and embodiments described herein in any combination.

A sixth aspect of the invention is a process for producing a composition comprising (i) a virus-like particle, wherein said virus-like particle is a virus-like particle of an RNA bacteriophage, and (ii) an oligonucleotide, wherein said oligonucleotide is packaged into said virus-like particle, said process comprising the steps of: (a) providing coat protein of said RNA bacteriophage; (b) providing an oligonucleotide, wherein preferably said oligonucleotide comprises a relative peak start time of 50 to 110%, said providing comprising the steps of: (i) providing an oligonucleotide in solution II, wherein said solution II comprises pH 5 to 8 and a cation, wherein preferably the concentration of said cation in said solution II is at least 20 mM, and wherein preferably said cation is selected from the group consisting of $Na^+$, $K^+$, $NH_4^+$, $Li^+$, $Ca^{2+}$, and $Mg^{2+}$; (ii) adjusting the temperature of solution II to temperature III wherein said temperature III is 50 to 99° C.; and (iii) incubating said oligonucleotide in solution II at temperature III, wherein said incubating is performed until said oligonucleotide comprises a relative peak start time of 50 to 110%; and (iv) adjusting the temperature of solution II to temperature IV, wherein said temperature IV is below 50° C.; wherein steps (i) to (iv) are preferably performed in the given order; (c) generating a mixture, wherein said mixture comprises: (i) said coat protein; (ii) an agent capable of preventing the self-assembly of said coat protein; (iii) said oligonucleotide; (d) removing said agent from said mixture; and (e) allowing said coat protein to self assemble into a virus-like particle. Said process may comprise any one of the features and embodiments described herein in any combination.

A seventh aspect of the invention is a process for producing a composition comprising (i) a virus-like particle, wherein said virus-like particle is a virus-like particle of an RNA bacteriophage, and (ii) an oligonucleotide, wherein said oligonucleotide is packaged into said virus-like particle, said process comprising the steps of: (a) providing coat protein of said RNA bacteriophage; (b) providing an oligonucleotide, wherein preferably said oligonucleotide comprises a relative peak start time of 50 to 110%, said providing comprising the steps of: (i) providing an oligonucleotide in solution I, wherein said oligonucleotide at least one poly G stretch; and wherein said solution I comprises an alkaline pH; (ii) disaggregating said oligonucleotide, wherein said disaggregating comprises the steps of: (1) adjusting the temperature of solution I to temperature I, wherein said temperature I is 4 to 70° C.; (2) incubating said oligonucleotide in said solution I at said temperature I, wherein said incubating is performed until said oligonucleotide comprises a relative peak start time above 110%; and (3) adjusting the temperature of said solution I to temperature II, wherein said temperature II is 0 to 70° C.; (iii) adjusting the pH of said solution I to pH 5 to 8; and (iv) aggregating said oligonucleotide, wherein said aggregating comprises the steps of: (1) providing said oligonucleotide in solution II, wherein said solution II comprises pH 5 to 8 and a cation, wherein preferably the concentration of said cation in said solution II is at least 20 mM, and wherein preferably said cation is selected from the group consisting of $Na^+$, $K^+$, $NH_4^+$, $Li^+$, $Ca^{2+}$, and $Mg^{2+}$; (2) adjusting the temperature of solution II to temperature III, wherein said temperature III is 50 to 99° C.; (3) incubating said oligonucleotide in solution II at temperature III, wherein said incubating is performed until said oligonucleotide comprises a relative peak start time of 50 to 110%; and (4) adjusting the temperature of solution II to temperature IV, wherein said temperature IV is below 50° C.; wherein steps (i) to (iv) are preferably performed in the given order; (c) generating a mixture, wherein said mixture comprises: (i) said coat protein; (ii) an agent capable of preventing the self-assembly of said coat protein; (iii) said oligonucleotide; (d) removing said agent from said mixture; and (e) allowing said coat protein to self assemble into a virus-like particle. Said process may comprise any one of the features and embodiments described herein in any combination.

An eighth aspect of the invention is the use of a nucleotide composition obtainable by any one of the processes of the invention, in a process for producing a composition comprising (i) a virus-like particle, wherein said virus-like particle is a virus-like particle of an RNA bacteriophage, and (ii) an oligonucleotide, wherein said oligonucleotide is packaged into said virus-like particle.

A ninth aspect of the invention is a composition obtainable by any one of the processes of the invention, said composition comprising (i) a virus-like particle, wherein said virus-like particle is a virus-like particle of an RNA bacteriophage, and (ii) an oligonucleotide, wherein said oligonucleotide is packaged into said virus-like particle, wherein preferably said RNA bacteriophage is Qβ, and wherein further preferably said oligonucleotide is G8-8 (SEQ ID NO:6) or G10 (SEQ ID NO:8), preferably G10 (SEQ ID NO:8), and wherein still further preferably the purity of said composition is at least at least 98%, more preferably at least 99%, and most preferably at least 99.2%.

DETAILED DESCRIPTION OF THE INVENTION

Figure 1:
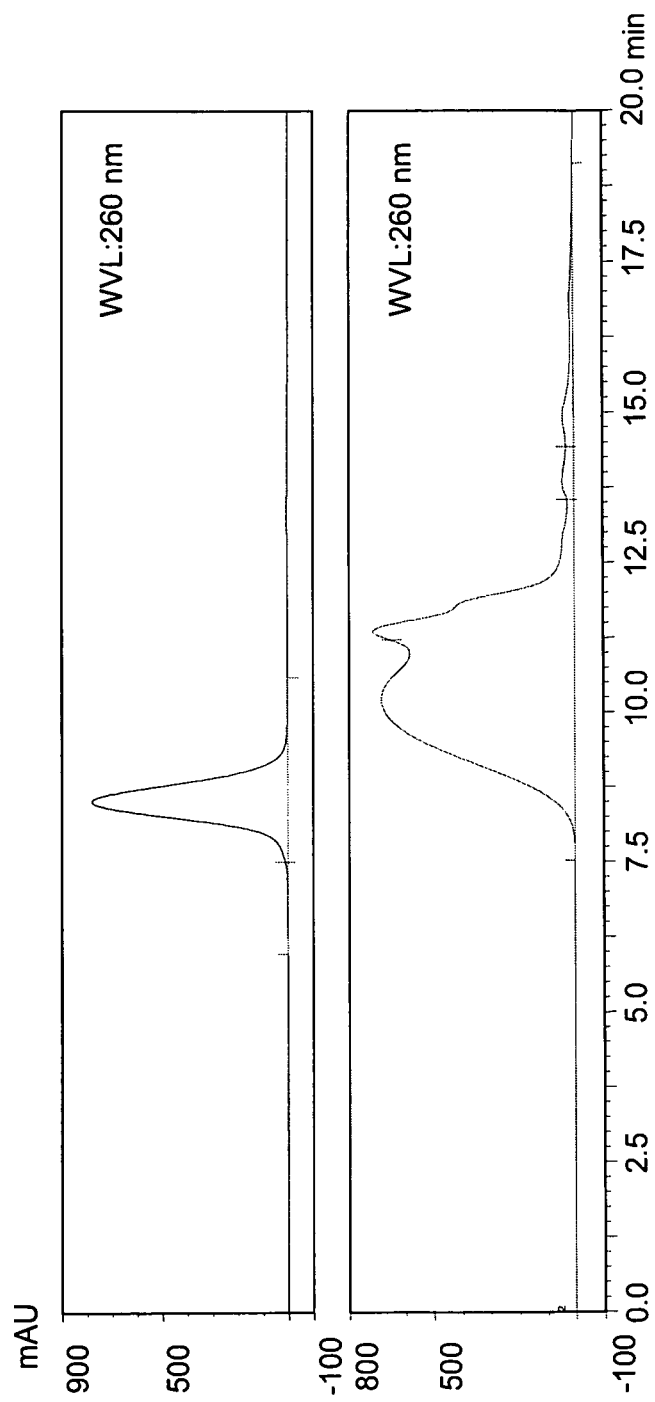
FIG. 1: Size exclusion HPLC chromatogram of the Qβ capsid standard (top) and aggregated G10 (bottom). HPLC was performed as described in Example 4. The retention time of the standard was 8.532 min, the peak start time of aggregated G10 was 7.510 min. Thus, the relative peak start time of the aggregated G10 was 88% (7.510 min/8.532 min*100).

The definitions and embodiments described in the following are, unless explicitly stated otherwise, applicable to any one of the aspects, and embodiments, in particular processes, compositions, nucleotide compositions and uses of the invention. Unless defined otherwise, all technical and scientific terms used herein have the same meanings as commonly understood by one of ordinary skill in the art to which this invention belongs.

"oligonucleotide": The term oligonucleotide as used herein refers to a single stranded deoxyribonucleotide. A preferred oligonucleotide comprises at least one poly G stretch as defined below. More preferred oligonucleotides comprise 2, 3, 4, 5, 6, 7, 8, 9, or 10 of said poly G stretches. Very preferred oligonucleotides comprise exactly two poly G stretches, wherein preferably one of said two poly G stretches is located at the 5' end or at the 3' end of said oligonucleotide. Even more preferred oligonucleotides comprise exactly two poly G stretches, wherein one of said two poly G stretches is located at the 5' end of said oligonucleotide and one of said two poly G stretches is located at the 3' end of said oligonucleotide. Typically and preferably, an oligonucleotide as used herein consists of 6 to 1000, preferably of 10 to 1000, more preferably of 10 to 200, still more preferably of 10 to 100, still more preferably of 20 to 40, and most preferably of 30 nucleotides. Further preferred oligonucleotides consist of 15, 16, 17, 18, 19, 20, 21, 22, 23, 24, 25, 26, 27, 28, 29, 30, 31, 32, 33, 34, 35, 36, 37, 38, 39, or 40 nucleotides. Still more preferred oligonucleotides consists of 24 to 32 nucleotides, more preferably of about 30 nucleotides.

The term oligonucleotide also refers to molecules comprising at least one modified nucleotide, wherein preferably said modified nucleotide is selected from (a) a nucleotide analogue or (b) a nucleotide comprising a backbone modification. In one embodiment the oligonucleotide comprises at least one modified nucleotide selected from the group consisting of (a) peptide nucleic acid, (b) inosin, (c) tritylated bases, (d) phosphorothioates, (e) alkylphosphorothioates, (f) 5-nitroindole desoxyribofuranosyl, (g) 5-methyldesoxycytosine, and (h) 5,6-dihydro-5,6-dihydroxydesoxythymidine. In a further embodiment the oligonucleotide comprises or alternatively consists of phosphothioated nucleotides. Phosphothioated nucleotides are protected against degradation in a cell or an organism and are therefore preferred nucleotide modifications. Further preferred are chemically, enzymatically or metabolically modified forms of polynucleotides as typically found in nature. However, preferred oligonucleotides exclusively consists of unmodified nucleotides, i.e. of adenosine, tymidine, guanosine, and/or cytidine. Still further preferred oligonucleotides exclusively consists of phosphodiester bound nucleotides.

Very preferred oligonucleotides are unmethylated CpG containing oligonucleotides comprising at least one, preferably one, two, three or four CpG motifs. Still more preferred oligonucleotides comprise a palindromic sequence, wherein preferably said palindromic sequence comprises least one, preferably one, two, three or four CpG motifs. Still more preferred oligonucleotides comprise a palindromic sequence, wherein preferably said palindromic sequence comprises, or preferably consists of the sequence GACGATCGTC (SEQ ID NO:1). Still more preferred oligonucleotides comprise a palindromic sequence, wherein said palindromic sequence is flanked at its 5' end by a poly G stretch and wherein said palindromic sequence is flanked at its 3' end by a poly G stretch, wherein preferably said palindromic sequence is GACGATCGTC (SEQ ID NO:1). Very preferred oligonucleotides comprise a palindromic sequence, wherein said palindromic sequence is flanked at its 5' end by at least 3 to 10, preferably by 4 to 10 guanosine entities and wherein said palindromic sequence is flanked at its 3' end at least 3 to 10, preferably by 4 to 10, guanosine entities, wherein preferably said palindromic sequence is GACGATCGTC (SEQ ID NO:1).

"poly G stretch": The term poly G stretch relates to a segment of an oligonucleotide, wherein said segment consists of at least 3 consecutive guanosine residues. Preferred poly G stretches consist of 3 to 25, preferably of 4 to 20, more preferably of 4 to 15 and most preferably of 4 to 10 consecutive guanosine entities. Further preferred poly G stretches consist of 3, 4, 5, 6, 7, 8, 9, 10, 11, 12, 13, 14, 15, 16, 17, 18, 19, or 20 consecutive guanosine entities.

"CpG motif": As used herein, the term "CpG motif" refers to short DNA sequence, preferably a single stranded DNA sequence, comprising a cytosine (C)— guanosine (G) dinucleotide, wherein C is unmethylated and wherein preferably said CG dinucleotide is phosphodiester bound. Preferably, a CpG motif comprises at least one, preferably one, two or three, additional nucleotides 5' and/or 3' of said CG dinucleotide, wherein further preferably said additional nucleotides do not comprise a CG dinucleotide.

"relative peak start time": The term "relative peak start time" is a parameter which is indicative of the aggregation state of an oligonucleotide. The relative peak start time of an oligonucleotide is determined by analytical size exclusion HPLC, wherein preferably said HPLC is performed essentially with, preferably exactly with the following parameters:

| | |
|---|---|
| Column: | TSKgel 5000 PWXL 7.8 mm * 30.0 cm (Lot: 5PWX06GNMH3304, Art: 08023, Tosoh Bioscience) |
| Eluent: | PBS (150 mM NaCl in 20 mM sodium phosphate buffer, pH 7.2) |
| Injection volume: | 40.0 µl (preferably comprising a concentration of about 20 µM to about 500 µM) |
| Flow rate: | 0.8 ml/min |
| Gradient: | Isocratic |
| Run time: | 20 min |
| Wavelength: | 215, 260 and 280 nm, data evaluation at 260 nm |
| Column oven temp.: | 25° C. |
| Autosampler temp.: | 8° C.; | and wherein the capsid of said RNA bacteriophage is used as a standard. The relative peak start time X % of said oligonucleotide relative to the capsid of said RNA bacteriophage is calculated as follows: X %=peak start time [min] of the oligonucleotide divided by the retention time of the standard [min]×100%, wherein the peak start time of the oligonucleotide is determined as the time when the elution of the oligonucleotide becomes detectable, and wherein the retention time of the standard is determined as the time of the occurrence of the maximum peak of said standard. Thus, in an embodiment wherein said RNA bacteriophage is, for example, bacteriophage AP205, capsid of AP205 is used as standard in said HPLC and the relative peak start time of said oligonucleotide is calculated relative to said AP205 standard. Importantly, in embodiments which do not refer to an RNA bacteriophage, the relative peak start time is always determined by using the capsid of bacteriophage Qβ as standard. Furthermore, in case of any uncertainty regarding the choice of the appropriate standard in said HPLC, capsid of bacteriophage Qβ is used as standard and the relative peak start time is determined relative to said capsid of bacteriophage Qβ. Thus, in a very preferred embodiment said relative peak start time is determined by said HPLC, wherein preferably said standard is capsid of bacteriophage Qβ, and wherein further preferably said relative peak start time is determined relative to said capsid of bacteriophage Qβ.

"packaged": The term "packaged" as used herein refers to the state of an oligonucleotide, in relation to the virus-like particle. The use of the terms "oligonucleotide packaged into VLP" or "VLP packaged with oligonucleotide" is equivalent. The term "packaged" as used herein refers to non-covalent binding, preferably to ionic interactions, hydrophobic interactions, or hydrogen bonds. Very preferably, the term "packaged" as used herein refers to the enclosement, or partial enclosement, of said oligonucleotide within the VLP. For example, the oligonucleotide, preferably the oligonucleotide comprising a relative peak start time of 50 to 110%, can be enclosed by the VLP without the existence of an actual binding, neither covalently nor non-covalently, or with a non-covalent binding. Typically and preferably, a VLP packaged with oligonucleotide protects said oligonuclaotide from degradation, preferably from DNAse hydrolysis. Therefore, in the preferred meaning, the term "packaged" indicates that the oligonucleotide in a packaged state is not accessible to DNAse hydrolysis. More preferably, the term "packaged" indicates that the oligonucleotide is not accessible to DNAse hydrolysis, wherein further preferably the DNAse is DNAseI or Benzonase. Still more preferably, the term "packaged" indicates that the oligonucleotide is not accessible to Benzonase hydrolysis.

The accessibility of the oligonucleotide for DNAse (e.g. DNaseI or Benzonase) is preferably assayed as described in Examples 11-17 of WO2003/024481A2 (see p. 111 therein). In a preferred meaning, a VLP is regarded as being packaged with an oligonucleotide, when after treatment with Benzonase (190 U Benzonase/mg coat protein in a buffer comprising 2 mM $MgCl_2$, pH 7.2, 20-25° C., 18 h) at least 90%, preferably at least 95%, most preferably at least 98% of said oligonucleotide can be recovered from said VLP (e.g. in an ethidiumbromide stained gel). It is apparent for the artisan that such assays require appropriate controls and may need to be adapted to the specific combination of VLP and oligonucleotide. In a more preferred meaning, an oligonucleotide is regarded as being packaged into a VLP of an RNA bacteriophage, when after treatment with Benzonase (190 U Benzonase/mg coat protein in a buffer comprising 2 mM MgCl2, pH 7.2, 20-25° C., 18 h) at least 90%, preferably at least 95%, most preferably at least 98% of said oligonucleotide can be recovered from said VLP of an RNA bacteriophage. In a very preferred meaning, oligonucleotide G10 (SEQ ID NO:8) is regarded as being packaged into a VLP of an RNA bacteriophage, when after treatment with Benzonase (190 U Benzonase/mg coat protein in a buffer comprising 2 mM $MgCl_2$, pH 7.2, 20-25° C., 18 h) at least 90%, preferably at least 95%, most preferably at least 98% of said G10 can be recovered from said VLP. In more specific meaning, oligonucleotide G10 (SEQ ID NO:8) is regarded as being packaged into a VLP of a RNA bacteriophage Qβ, AP205, GA or fr, when after treatment with Benzonase (190 U Benzonase/mg coat protein in a buffer comprising 2 mM MgCl$_2$, pH 7.2, 20-25° C., 18 h) at least 90%, preferably at least 95%, most preferably at least 98% of said G10 can be recovered from said VLP of an RNA bacteriophage. In a very specific meaning, oligonucleotide G10 (SEQ ID NO:8) is regarded as being packaged into a VLP of a RNA bacteriophage Qβ, when after treatment with Benzonase (190 U Benzonase/mg coat protein in a buffer comprising 2 mM MgC12, pH 7.2, 20-25° C., 18 h) at least 90%, preferably at least 95%, most preferably at least 98% of said unmethylated CpG-containing oligonucleotide can be recovered from said VLP of RNA bacteriophage Qβ.

"coat protein": As used herein, the term "coat protein" refers to the protein(s) of a RNA bacteriophage capable of being incorporated within the capsid assembly of the bacteriophage or the RNA bacteriophage. Thus, the term coat protein refers to the protein forming the capsid of a RNA bacteriophage or a VLP of a RNA bacteriophage. Typically and preferably, coat protein of RNA bacteriophages has a dimeric structure.

"fragment of a (recombinant) coat protein", in particular fragment of a recombinant coat protein, as used herein, is defined as a polypeptide, which is of at least 70%, preferably at least 80%, more preferably at least 90%, even more preferably at least 95% the length of the wild-type coat protein, or wild type recombinant protein, respectively and which preferably retains the capability of forming VLP. Preferably the fragment is obtained by at least one internal deletion, at least one truncation or at least one combination thereof. The term "fragment of a recombinant coat protein" or "fragment of a coat protein" shall further encompass polypeptide, which has at least 80%, preferably 90%, even more preferably 95% amino acid sequence identity with the wildtype coat protein, respectively, and which is preferably capable of assembling into a virus-like particle. The term "mutant coat protein" refers to a polypeptide having an amino acid sequence derived from the wild type recombinant protein, or coat protein, respectively, wherein the amino acid sequence is at least 80%, preferably at least 85%, 90%, 95%, 97%, or 99% identical to the wild type sequence and preferably retains the ability to assemble into a VLP.

"virus-like particle (VLP)", as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. Preferably a virus-like particle in accordance with the invention is non-replicative and/or non-infectious since it lacks all or part of the viral genome or genome function. In one embodiment, a virus-like particle is a virus particle, in which the viral genome has been physically or chemically inactivated, removed by disassembly and reassembly, or by assembly of purified proteins into a VLP. Typically and more preferably a virus-like particle lacks all or part of the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, preferably RNA bacteriophage. The term "capsid", refers to a macromolecular assembly composed of viral protein subunits. Typically, there are 60, 120, 180, 240, 300, 360 and more than 360 viral protein subunits. Typically and preferably, the interactions of these subunits lead to the formation of viral capsid with an inherent repetitive organization, wherein said structure typically and preferably is spherical. For example, the capsids of RNA bacteriophages have a spherical form of icosahedral symmetry.

"virus-like particle of an RNA bacteriophage": As used herein, the term "virus-like particle of a RNA bacteriophage" refers to a virus-like particle comprising, or preferably consisting essentially of or consisting of coat proteins, mutants or fragments thereof, of a RNA bacteriophage. In addition, virus-like particle of a RNA bacteriophage resembling the structure of a RNA bacteriophage, being non replicative and/or non-infectious, and lacking at least the gene or genes encoding for the replication machinery of the RNA bacteriophage, and typically also lacking the gene or genes encoding the protein or proteins responsible for viral attachment to or entry into the host. Preferred VLPs derived from RNA bacteriophages exhibit icosahedral symmetry and consist of 180 subunits. In the context of the invention the term virus-like particle of an RNA bacteriophage preferably relates to a macromolecular structure obtained by the self-assembly of recombinant coat protein of an RNA bacteriophage, or fragments or mutants thereof, wherein preferably said self-assembly took place in the presence of and oligonucleotide.

"agent capable of preventing the self assembly of coat protein": An agent capable of preventing the self assembly of coat protein is an agent which prevents the spontaneous formation of virus-like particles in said mixture. The artisan is able to determine the chemical nature and the appropriate concentration of said agent experimentally, e.g. by analyzing said mixture by size exclusion chromatography as disclosed in Example 9. An agent is capable of preventing the self assembly of coat protein, when after incubation of said mixture for at least 1 h at room temperature, preferably at 22° C., no virus-like particle is detectable by the size exclusion chromatography disclosed in Example 9. However, agent which is capable of preventing the self assembly of coat protein, does not irreversibly modify said coat protein and removing said agent from said mixture will result in the spontaneous formation of virus-like particles. Preferred agents capable of preventing the self assembly of coat protein comprise detergents, guanidiniumhydrochloride and urea, most preferably urea. Preferred detergents are sodiumdodecylsulfate, Tween 20, TritonX 100 and the like. Typically and preferably agents capable of preventing the self assembly of coat protein further comprise a reducing agent which keeps intermolecular disulfide bounds formed by cystein residues of said coat protein in a reduced state.

"protein yield": The protein yield of a process of the invention is determined as the amount of coat protein recovered as virus-like particle after the last step of said process relative to the amount of coat protein contained in said mixture, wherein preferably the amount of said coat protein is determines by Bradford protein assay. Typically and preferably at least 70%, preferably at least 75% of the coat protein contained in said mixture is recovered as virus-like particle after the final step of said process, wherein preferably said final step is said sterile filtrating.

"oligonucleotide yield": The oligonucleotide yield of a process of the invention is determined as the amount of oligonucleotide that can be recovered from said virus-like particle after the last step of said process relative to the amount of said oligonucleotide contained in said mixture, wherein preferably the amount of said oligonucleotide recovered from said virus-like particle is determined essentially or preferably exactly as disclosed in Example 9. Typically and preferably at least 70%, preferably at least 75% of the oligonucleotide contained in said mixture is recovered from said virus-like particle after the final step of said process, wherein preferably said final step is said sterile filtrating.

"purity": The purity of a composition of the invention comprising (i) a virus-like particle, wherein said virus-like particle is a virus-like particle of an RNA bacteriophage, and (ii) an oligonucleotide, wherein said oligonucleotide is packaged into said virus-like particle, is determined by analytic size exclusion HPLC, wherein said HPLC is performed under conditions essentially, preferably exactly as disclosed in Example 4. The purity of said composition is determined as the percentage of the peak area of said virus-like particle contained in said composition relative to the total peak area of the same chromatogram. Typically and preferably the purity of a composition of the invention is at least 98%, preferably at least 99%.

"one", "a/an": When the terms "one," "a," or "an" are used in this disclosure, they mean "at least one" or "one or more," unless otherwise indicated.

"about": within the meaning of the present application the expression about shall have the meaning of +/−10%. For example about 100 shall mean 90 to 110.

The invention provides processes for producing a nucleotide composition comprising an aggregated oligonucleotide. In more detail, the invention provides a process for producing a nucleotide composition comprising an oligonucleotide, wherein preferably said oligonucleotide comprises a relative peak start time of 50 to 110%, said process comprising the steps of: (a) providing an oligonucleotide in a solution II, wherein said oligonucleotide preferably comprises at its 5' end at least 3 guanosine entities and at its 3' end at least 3 guanosine entities; and wherein said solution II comprises a pH of 5 to 8; and wherein said solution II comprises a cation, wherein preferably the concentration of said cation in said solution II is at least 20 mM, wherein said cation is preferably selected from the group consisting of $Na^+$, $K^+$, $NH_4^+$, $Li^+$, $Ca^{2+}$, and $Mg^{2+}$; (b) adjusting the temperature of solution II to temperature III wherein said temperature III is 50 to 99° C.; and (c) incubating said oligonucleotide in solution II at temperature III, wherein said incubating is performed until said oligonucleotide comprises a relative peak start time of 50 to 110%; and (d) adjusting the temperature of solution II to temperature IV, wherein said temperature IV is below 50° C.; wherein said steps are preferably performed in the given order. All embodiments described in the following are applicable to this process in any combination.

As mentioned above, it was found that it is advantages to subject said oligonucleotide to a disaggregation step prior to said aggregation step, wherein preferably said oligonucleotide is completely disaggregated. Complete disaggregation of the oligonucleotide means that the apparent molecular weight of the oligonucleotide in size exclusion HPLC, preferably carried out essentially as described in Example 4, corresponds to the molecular weight which can be derived from the sequence of said oligonucleotide. Thus, the invention further provides a process for producing a nucleotide composition comprising an oligonucleotide, wherein preferably said oligonucleotide comprises a relative peak start time of 50 to 110%, said process comprising the steps of: (a) providing an oligonucleotide in solution I, wherein said oligonucleotide at least one poly G stretch; and wherein said solution I comprises an alkaline pH; (b) disaggregating said oligonucleotide, wherein said disaggregating comprises the steps of: (i) adjusting the temperature of solution I to temperature I, wherein said temperature I is 4 to 70° C.; (ii) incubating said oligonucleotide in said solution I at said temperature I, wherein said incubating is performed until said oligonucleotide comprises a relative peak start time above 110%; and (iii) adjusting the temperature of said solution I to temperature II, wherein said temperature II is 0 to 70° C.; (c) adjusting the pH of said solution I to pH 5 to 8; and (d) aggregating said oligonucleotide, wherein said aggregating comprises the steps of: (i) providing said oligonucleotide in solution II, wherein said solution II comprises pH 5 to 8 and a cation, wherein preferably the concentration of said cation in said solution II is at least 20 mM, and wherein preferably said cation is selected from the group consisting of $Na^+$, $K^+$, $NH_4^+$, $Li^+$, $Ca^{2+}$, and $Mg^{2+}$; (ii) adjusting the temperature of solution II to temperature III, wherein said temperature III is 50 to 99° C.; (iii) incubating said oligonucleotide in solution II at temperature III, wherein said incubating is performed until said oligonucleotide comprises a relative peak start time of 50 to 110%; and (iv) adjusting the temperature of solution II to temperature IV, wherein said temperature IV is below 50° C.; wherein said steps are preferably performed in the given order.

The disaggregation of untreated oligonucleotide which may comprise partially aggregated oligonucleotide occurs at alkaline pH. The disaggregation process can be facilitated by elevated temperature.

Thus, in one embodiment solution I comprises a pH of 8 to 13, preferably 10 to 13, most preferably 12. Solution I may comprise any buffer or agent may comprise any buffer or agent known in the art which allows to adjust the pH between 8 and 13. In a preferred embodiment solution I comprises hydroxide, preferably a metal hydroxide, most preferably a hydroxide of an alkali metal or an earth alkaline metal, preferably a hydroxide of an alkali metal. In a preferred embodiment said hydroxide is potassium hydroxide or sodium hydroxide, most preferably sodium hydroxide. In one embodiment the concentration of said hydroxide, preferably of said sodium hydroxide, in said solution I is 10 mM to 200 mM, more preferably about 25 mM, most preferably 25 mM.

To avoid degradation of the oligonucleotide, temperature I preferably does not exceed 90° C., temperature I does not exceed 70° C. In one embodiment temperature I is room temperature, preferably 19 to 25° C. In another embodiment temperature I is 4 to 70° C., preferably 20 to 70° C., more preferably 45 to 70° C., preferably about 50° C., and most preferably 50° C. In a preferred embodiment said incubating said oligonucleotide in said solution I at said temperature I is performed until said oligonucleotide is completely disaggregated. In another embodiment said incubating said oligonucleotide in said solution I at said temperature I is performed until the relative peak start time of said oligonucleotide is above 110%, preferably above 130% and most preferably above 135%. In a further embodiment said incubating said oligonucleotide in said solution I at said temperature I is performed for 30 to 190 min, preferably for 50 to 90 min, most preferably for 70 min.

In a further preferred embodiment the concentration of said oligonucleotide in said solution I is 50 µM to 2 mM, preferably 50 to 500 µM, more preferably 200 to 300 µM, and most preferably 260 µM.

The disaggregation of the oligonucleotide can be terminated by neutralizing or acidifying solution I and/or reducing the temperature. Thus, said process further comprises the step of adjusting the pH of said solution I to pH 8 or below, preferably to pH 5 to 8. In a preferred embodiment said adjusting of the pH is performed until said pH is 6 to 7, most preferably until said pH is about 6. In a further embodiment said adjusting of the pH of said solution I is performed by the addition of acid to said solution I. Any mineral or organic acid known in the art can be used for this purpose. In a preferred embodiment said acid is selected from the group consisting of phosphoric acid; hydrochloric acid; and organic acids, wherein said organic acids are preferably selected from formic acid, acetic acid, and citric acid. In a preferred embodiment said acid is a mineral acid. Preferably, said acid is phosphoric acid or hydrochloric acid, most preferably phosphoric acid.

Said process further comprises adjusting the temperature of said solution I to temperature II, wherein preferably said temperature II is 0 to 70° C. and wherein preferably said temperature II is below temperature I. In a preferred embodiment said temperature II is 0 to 25° C., preferably 0 to 10° C., and most preferably 0 to 2° C.

The process further comprises the step of aggregating said oligonucleotide. Aggregation of the oligonucleotide is achieved by incubating said oligonucleotide at about neutral pH in a solution comprising cations capable of supporting the formation of G-quadruplex DNA structures (cf. Simonsson T., Biol. Chem. 382:621-628) and at a temperature above 50° C. Thus, in one embodiment said cation is selected from the group consisting of $Na^+$, $K^+$, $Rb^+$, $NH_4^+$, $Cs^+$, $Li^+$, $Sr^{2+}$, $Ba^{2+}$, $Ca^{2+}$, $Mn^{2+}$, $Ni^{2+}$, and $Mg^{2+}$. In a preferred embodiment said cation is selected from the group consisting of $Na^+$, $K^+$, $NH_4^+$, $Li^+$, $Ca^{2+}$, and $Mg^{2+}$, more preferably said cation is $Na^+$ or $K^+$, most preferably said cation is $Na^+$. In a very preferred embodiment the concentration In a preferred embodiment solution II comprising said oligonucleotide is obtained by the addition of said cation to said solution I, wherein preferably said addition is performed after said adjusting of the pH of solution I.

In a further embodiment said solution II a mixture of any cation selected from the group consisting of $Na^+$, $K^+$, $Rb^+$, $NH_4^+$, $Cs^+$, $Li^+$, $Sr^{2+}$, $Ba^{2+}$, $Ca^{2+}$, $Mn^{2+}$, $Co^{2+}$, $Ni^{2+}$, and $Mg^{2+}$. In a further embodiment said solution II a mixture of any cation selected from the group consisting of $Na^+$, $K^+$, $NH_4^+$, $Li^+$, $Ca^{2+}$, and $Mg^{2+}$. In a very preferred embodiment said mixture comprises or preferably consists of $Na^+$ and K.

In a preferred embodiment said solution II comprises at least 20 mM, preferably at least 100 mM, more preferably 200 to 275 mM, and most preferably 250 mM of said cation or of said mixture of cations. In a very preferred embodiment said solution II comprises 250 mM of $Na^+$ and $K^+$, most preferably 250 mM of $Na^+$. In still further preferred embodiment said solution II comprises 250 mM of sodium chloride or potassium chloride, most preferably 250 mM of sodium chloride. However, any sodium, potassium, ammonium, lithium, calcium or magnesium salt known in the art can be used for this purpose.

In a further embodiment the concentration of said oligonucleotide in said solution II is 50 μM to 2 mM, preferably 100 to 300 μM most preferably 175 μM.

In a further embodiment said process further comprises adjusting the temperature of solution II to temperature III, wherein said temperature III is 50 to 99° C., preferably 80 to 90° C., more preferably about 85° C., and most preferably 85° C.

In a further embodiment said process comprises incubating said oligonucleotide in solution II at temperature III, wherein said incubating is performed until said oligonucleotide comprises a relative peak start time of 50 to 110%, preferably of 80 to 95%, more preferably of 80 to 90%, still more preferably of 83 to 90%, still more preferably of 85 to 90%, and most preferably of 88%. In a very preferred embodiment said oligonucleotide is G10 (SEQ ID NO:8) and said incubating is performed until said oligonucleotide comprises a relative peak start time of 50 to 110%, preferably of 80 to 95%, more preferably of 80 to 90%, still more preferably of 83 to 90%, still more preferably of 85 to 90%, and most preferably of 88%.

The incubation time required to obtain oligonucleotide comprising the desired relative peak start time depends on the sequence and the purity of the oligonucleotide and ranges typically and preferably from about 5 min to about 30 min. In a preferred embodiment said oligonucleotide is G10 (SEQ ID NO:8) and said incubating of said oligonucleotide in said solution II at said temperature III is performed for 9 to 24 min.

The aggregation process is terminated by cooling solution II below 50° C. In a preferred embodiment said process comprises adjusting the temperature of solution II to temperature IV, wherein said temperature IV is below 50° C., and wherein preferably said temperature IV is 0 to 25° C., more preferably 0 to 10° C., and most preferably 0 to 2° C.

It has been found that the heating and/or cooling rates applied in the process of the invention have impact on yield and particle size distribution of the aggregated oligonucleotide obtained. In particular, it was found in the course of up-scaling of the process to higher batch volumes, that yield and particle size distribution can be further improved by using temperature ramps (i.e. heating or cooling rates) of at least 3.6° C./min. The artisan can achieve a defined temperature ramp by standardizing the process conditions with respect to the reaction volume, geometry and heat conductivity of the reaction vessel and the temperature difference chosen. In a preferred embodiment, said adjusting the temperature of solution I to temperature I, said adjusting the temperature of said solution I to temperature II, said adjusting the temperature of solution II to temperature III, and/or said adjusting the temperature of solution II to temperature IV are performed with a temperature ramp of least 3.6° C./min. In a further preferred embodiment, said adjusting the temperature of solution II to temperature III, is performed with a temperature ramp of least 3.6° C./min, wherein preferably said temperature ramp is about 7° C./min. In a further preferred embodiment, said adjusting the temperature of solution II to temperature IV is performed with a temperature ramp of least 3.6° C./min, wherein preferably said temperature ramp is about 7° C./min.

In order to be capable of forming aggregates, said oligonucleotide comprises at least one, preferably two poly G stretches. In a preferred embodiment said oligonucleotide comprises at its 5' end at least 3, preferably at least 4 guanosine entities and at its 3' end at least 3, preferably at least 4 guanosine entities. In a further preferred embodiment said oligonucleotide comprises at its 5' end at least 4 guanosine entities and at its 3' end at least 4 guanosine entities. In a preferred embodiment said oligonucleotide comprises at its 5' end at least 3 and at most 20, preferably at most 15 guanosine entities and at its 3' end at least 3 and at most 20, preferably at most 15 guanosine entities. In a further preferred embodiment said oligonucleotide comprises at its 5' end at least 3, preferably at least 4, and at most 11 guanosine entities and at its 3' end at least 3, preferably at least 4 and at most 10 guanosine entities. In a further preferred embodiment said oligonucleotide is an unmethylated CpG containing oligonucleotide, preferably wherein said unmethylated CpG containing oligonucleotide comprises two poly G stretches, wherein preferably each of said poly G stretches consists of at least 4 guanosine entities, and wherein further preferably said unmethylated CpG containing oligonucleotide comprises a palindromic sequence, wherein said palindromic sequence is located between said poly G stretches. In a further preferred embodiment said oligonucleotide comprises at its 5' end at least 3, preferably at least 4 guanosine entities and at its 3' end at least 3, preferably at least 4 guanosine entities, wherein said oligonucleotide further comprises a palindromic sequence, wherein preferably said palindromic sequence is GAC-GATCGTC (SEQ ID NO:1).

In a further preferred embodiment said oligonucleotide comprises a palindromic sequence, wherein preferably said palindromic sequence is GACGATCGTC (SEQ ID NO:1), and wherein said palindromic sequence is flanked at its 5' end by at least 3, preferably at least 4, and at most 15 guanosine entities and wherein said palindromic sequence is flanked at its 3' end by at least 3, preferably at least 4, and at most 15 guanosine entities.

In a further preferred embodiment said oligonucleotide comprises 10 to 1000 nucleotides, preferably 10 to 200 nucleotides, more preferably 10 to 100 nucleotides, still more preferably 20 to 40 nucleotides, most preferably 30 nucleotides.

In a very preferred embodiment said oligonucleotide comprises or preferably consists of a nucleic acid sequence selected from the group consisting of: (a) "G4-4" GGGG-GACGAT CGTCGGGG (SEQ ID NO:2); (b) "G5-5" GGGGGGACGA TCGTCGGGGG (SEQ ID NO:3); (c) "G6-6" GGGGGGGACG ATCGTCGGGG GG (SEQ ID NO:4); (d) "G7-7" GGGGGGGGAC GATCGTCGGG GGGG (SEQ ID NO:5); (e) "G8-8" GGGGGGGGGA CGATCGTCGG GGGGGG (SEQ ID NO:6); (f) "G9-9" GGGGGGGGGG ACGATCGTCG GGGGGGGG (SEQ ID NO:7); (g) "G10" GGGGGGGGGG GACGATCGTC GGGGGGGGGG (SEQ ID NO:8); (h) "G11" GGGGGGGGGG GGACGATCGT CGGGGGGGGG GG (SEQ ID NO:9), wherein preferably said oligonucleotide entirely consists of phosphodiester bound nucleotides. In a still more preferred embodiment said oligonucleotide comprises or preferably consists of the nucleic acid sequence "G10" GGGGGGGGGGGGACGATCGTCGGGGGGGGGG (SEQ ID NO:8), wherein preferably said oligonucleotide entirely consists of phosphodiester bound nucleotides.

The invention further relates to a nucleotide composition comprising an oligonucleotide, wherein said nucleotide composition is obtainable by any one of the processes described above, implementing any one of the embodiments described above, alone or in any combination. In particular, the invention relates to a nucleotide composition comprising an oligonucleotide, wherein said nucleotide composition is obtainable by any one of the processes described above, wherein preferably said oligonucleotide comprises a relative peak start time of 50 to 110%, preferably of 80 to 95%, more preferably of 80 to 90%, still more preferably of 83 to 90%, still more preferably of 85 to 90%, and most preferably of 88%. In a preferred embodiment, said nucleotide composition comprises an oligonucleotide, wherein said oligonucleotide comprises or preferably consists of a nucleic acid sequence selected from the group consisting of: (a) "G4-4" GGGGGACGAT CGTCGGGG (SEQ ID NO:2); (b) "G5-5" GGGGGGACGA TCGTCGGGGG (SEQ ID NO:3); (c) "G6-6" GGGGGGGACG ATCGTCGGGG GG (SEQ ID NO:4); (d) "G7-7" GGGGGGGGAC GATCGTCGGG GGGG (SEQ ID NO:5); (e) "G8-8" GGGGGGGGGA CGATCGTCGG GGGGGG (SEQ ID NO:6); (f) "G9-9" GGGGGGGGGG ACGATCGTCG GGGGGGGG (SEQ ID NO:7); (g) "G10" GGGGGGGGGG GACGATCGTC GGGGGGGGGG (SEQ ID NO:8); (h) "G11" GGGGGGGGGG GGACGATCGT CGGGGGGGGG GG (SEQ ID NO:9), wherein preferably said oligonucleotide entirely consists of phosphodiester bound nucleotides. In a still more preferred embodiment said nucleotide composition comprises an oligonucleotide, wherein said oligonucleotide comprises or preferably consists of the nucleic acid sequence "G10" GGGGGGGGGGGGACGATCGTCGGGGGGGGGG (SEQ ID NO:8), wherein preferably said oligonucleotide entirely consists of phosphodiester bound nucleotides. In very preferred embodiment said nucleotide composition comprises an oligonucleotide, wherein said oligonucleotide consists of the nucleic acid sequence "G10" GGGGGGGGGGGGACGATCGTCGGGGGGGGGG (SEQ ID NO:8), wherein said oligonucleotide entirely consists of phosphodiester bound nucleotides, and wherein said oligonucleotide comprises a relative peak start time of 50 to 110%, preferably of 80 to 95%, more preferably of 80 to 90%, still more preferably of 83 to 90%, still more preferably of 85 to 90%, and most preferably of 88%.

As mentioned before, the nucleotide compositions of the invention are useful in a process for producing a composition comprising (i) a virus-like particle, wherein said virus-like particle is a virus-like particle of an RNA bacteriophage, and (ii) an oligonucleotide, wherein said oligonucleotide is packaged into said virus-like particle, because aggregated oligonucleotide as contained in the nucleotide compositions of the invention facilitates the self assembly of coat protein of RNA bacteriophages and, thus, the formation of virus-like particles of RNA bacteriophages, wherein said oligonucleotide is packages into said virus-like particles. The invention therefore further relates to a process for producing a composition comprising (i) a virus-like particle, wherein said virus-like particle is a virus-like particle of an RNA bacteriophage, and (ii) an oligonucleotide, wherein said oligonucleotide is packaged into said virus-like particle, said process comprising the steps of: (a) providing coat protein of said RNA bacteriophage; (b) providing a nucleotide composition comprising an oligonucleotide, wherein said nucleotide composition is a nucleotide composition obtainable by any one of the processes of the invention; (c) generating a mixture, wherein said mixture comprises: (i) said coat protein; (ii) an agent capable of preventing the self-assembly of said coat protein; (iii) said oligonucleotide; (d) removing said agent from said mixture; and (e) allowing said coat protein to self assemble into a virus-like particle. Said process may comprise any one of the features and embodiments described herein in any combination.

Oligonucleotide comprising a relative peak start time of 50 to 110% is most useful for the purpose of the invention, whereas oligonucleotide comprising a higher or lower relative peak start time may result in low yield. Thus, the invention further provides a process for producing a composition comprising (i) a virus-like particle, wherein said virus-like particle is a virus-like particle of an RNA bacteriophage, and (ii) an oligonucleotide, wherein said oligonucleotide is packaged into said virus-like particle, said process comprising the steps of: (a) providing coat protein of said RNA bacteriophage; (b) providing an oligonucleotide, (i) wherein said oligonucleotide preferably comprises at least one poly G stretch; and (ii) wherein said oligonucleotide comprise a relative peak start time of 50 to 110%; (c) generating a mixture, wherein said mixture comprises: (i) said coat protein; (ii) an agent capable of preventing the self-assembly of said coat protein; (iii) said oligonucleotide; (d) removing said agent from said mixture; and (e) allowing said coat protein to self assemble into a virus-like particle. Said process may comprise any one of the features and embodiments described herein in any combination.

The artisan is able to produce and to purify coat protein of RNA bacteriophages by purifying said coat protein from RNA bacteriophages by applying standard methods. However, in a preferred embodiment said coat protein is recombinantly produced, preferably by expression of said coat protein in *E. coli*. Methods for obtaining coat protein of RNA bacteriophages are disclosed in the Examples section. In a preferred embodiment said coat protein comprises, or alternatively essentially consists of, or alternatively consists of recombinant proteins, or fragments thereof, of a RNA bacteriophage, wherein preferably said RNA bacteriophage is selected from the group consisting of: (a) bacteriophage Qβ; (b) bacteriophage R17; (c) bacteriophage fr; (d) bacteriophage GA; (e) bacteriophage SP; (f) bacteriophage MS2; (g) bacteriophage M11; (h) bacteriophage MX1; (i) bacteriophage NL95; j) bacteriophage f2; (k) bacteriophage PP7; and bacteriophage AP205. In a preferred embodiment said RNA bacteriophage is bacteriophage Qβ. Processes and methods for expressing and purifying virus-like particles of RNA bacteriophages, in particular of bacteriophage Qβ are disclosed in WO2006/125821A2 and WO2007/039552A1, which are incorporated herein by way of reference. Coat protein of RNA bacteriophage can be obtained by disassembly of virus-like particles, e.g. as described in the Examples herein.

In a further preferred embodiment said RNA bacteriophage is bacteriophage AP205. Assembly-competent mutant forms of AP205 VLPs, including AP205 coat protein with the substitution of proline at amino acid 5 to threonine, may also be used in the practice of the invention. WO 2004/007538 describes, in particular in Example 1 and Example 2, how to obtain VLP comprising AP205 coat proteins, and hereby in particular their expression and purification. WO 2004/007538 is incorporated herein by way of reference.

In a further preferred embodiment said RNA bacteriophage is bacteriophage fr. Fr coat protein in the form of recombinant VLP may be obtained as described by Pushko P et al. ((1993) Prot Engin 6:883-891). In a further preferred embodiment said RNA bacteriophage is bacteriophage GA. GA VLP may be obtained by cloning GA coat protein cDNA isolated by reverse transcription from GA phage into pQb185, which is described for example in WO2004/007538. Disassembly of Fr and GA VLPs can be readily done by incubating the VLPs in 7 M urea, optionally supplemented with acetic acid at a concentration of 0.1 M. The nucleic acid is further purified from the coat protein by ion exchange chromatography, either at a pH where a significant amount of the coat protein flows through while the nucleic acid is retained, or at a pH where the coat protein is also adsorbed on the column and subsequently eluted with a salt gradient.

In one preferred embodiment, said coat protein comprises or preferably consists of an amino acid sequence selected from the group consisting of: (a) SEQ ID NO:10 (Qβ CP); (b) a mixture of SEQ ID NO:10 and SEQ ID NO:11 (Qβ A1 protein); (c) SEQ ID NO:12 (R17 coat protein); (d) SEQ ID NO:13 (fr coat protein); (e) SEQ ID NO:14 (GA coat protein); (f) SEQ ID NO:15 (SP coat protein); (g) a mixture of SEQ ID NO:15 and SEQ ID NO:16; (h) SEQ ID NO:17 (MS2 coat protein); (i) SEQ ID NO:18 (M11 coat protein); (j) SEQ ID NO:19 (MX1 coat protein); (k) SEQ ID NO:20 (NL95 coat protein); (l) SEQ ID NO:21 (f2 coat protein); (m) SEQ ID NO:22 (PP7 coat protein); and (n) SEQ ID NO:23 (AP205 coat protein). In a further preferred embodiment, aid coat protein comprises or preferably consists of an amino acid sequence selected from the group consisting of: (a) SEQ ID NO:10; (b) a mixture of SEQ ID NO:11 and SEQ ID NO:11; (c) SEQ ID NO:13; (d) SEQ ID NO:14; (e) SEQ ID NO:23. In a further very preferred embodiment said coat protein aid coat protein comprises or preferably consists of an amino acid sequence selected from the group consisting of: (a) SEQ ID NO:10; and (b) a mixture of SEQ ID NO:10 and SEQ ID NO:11.

Furthermore, mutant coat protein of bacteriophage Qβ wherein exposed lysine residues are replaced by arginines can be used for the present invention. Thus, in a further preferred embodiment said coat protein comprises, consists essentially of or alternatively consists of mutant Qβ coat proteins as disclosed WO02/056905 (cf. Example 18 therein).

Further RNA bacteriophage coat proteins have also been shown to self-assemble upon expression in a bacterial host (Kastelein, R A. et al., Gene 23:245-254 (1983), Kozlovskaya, T M. et al., Dokl. Akad. Nauk SSSR 287:452-455 (1986), Adhin, M R. et al., Virology 170:238-242 (1989), Priano, C. et al., J. Mol. Biol. 249:283-297 (1995)). In particular the biological and biochemical properties of GA (Ni, C Z., et al., Protein Sci. 5:2485-2493 (1996), Tars, K et al., J. Mol. Biol. 271:759-773 (1997)) and of fr (Pushko P. et al., Prot. Eng. 6:883-891 (1993), Liljas, L et al. J. Mol. Biol. 244:279-290, (1994)) have been disclosed. The crystal structure of several RNA bacteriophages has been determined (Golmohammadi, R. et al., Structure 4:543-554 (1996)).

Typically and preferably, the processes disclosed herein for producing a composition comprising (i) a virus-like particle, wherein said virus-like particle is a virus-like particle of an RNA bacteriophage, and (ii) an oligonucleotide, wherein said oligonucleotide is packaged into said virus-like particle are carried out at room temperature. In a preferred embodiment said processes are performed at 15 to 30° C., preferably at 19 to 25° C., most preferably at 22° C. In a further preferred embodiment said generating of said mixture, said removing said agent from said mixture, and/or said allowing said coat protein to self assemble into a virus-like particle is performed at 15 to 30° C., preferably at 19 to 25° C., most preferably at 22° C.

Said process comprises generating a mixture, wherein said mixture comprises: (i) said coat protein; (ii) an agent capable of preventing the self-assembly of said coat protein; (iii) said oligonucleotide. In a preferred embodiment the concentration of said coat protein in said mixture is 0.5 to 10 mg/ml, preferably 1 to 4 mg/ml, and most preferably 2.5 mg/ml, wherein preferably said concentration is determined in a Bradford assay. In a further preferred embodiment the concentration of said oligonucleotide in said mixture is 12.5 to 250 μM, more preferably 25 to 100 μM, and most preferably 62.5 μM.

In order to obtain optimal yield of the packaging process, the molar ratio of said oligonucleotide and of said coat protein in said mixture is 0.5 to 1.2, preferably 0.6 to 0.8 and most preferably 0.7. The use of less oligonucleotide per coat protein will lead to low yield while the use of an excessive overshoot of oligonucleotide increases costs and may result in a product with low purity. In a very preferred embodiment the concentration of said coat protein in said mixture is 2.5 mg/ml, and the concentration of said oligonucleotide in said mixture is 62.5 μM.

Coat proteins of viruses and in particular of RNA bacteriophages generally have a strong tendency to self assembly into a capsid structure, e.g. into a virus like particle. Though not in each case, this tendency is in many cases enhanced in the presence of nucleic acids such as RNA or DNA. In order to obtain optimal mixing of said coat protein and said oligonucleotide before the self assembly of said coat protein takes place, said mixture comprises an agent capable of preventing the self-assembly of said coat protein. Typically and preferably said agent comprises a denaturing compound. Numerous denaturing compounds are known in Biochemistry and include detergents, urea or guanidiniumhydrochloride. Preferred detergents are sodiumdodecylsulfate, Tween 20, TritonX 100 and the like. In a preferred embodiment said denaturing compound is urea or guanidiniumhydrochloride, wherein preferably the concentration of said denaturing compound, preferably of said urea, in said mixture is 0.25 to 7.2 M, preferably 1 M. In a very preferred embodiment said denaturing compound is urea, and the concentration of said urea in said mixture is 0.5 to 2 M, preferably 0.7 to 1.5 M, more preferably 0.8 to 1.2 M, and most preferably 1 M.

In a further preferred embodiment the pH of said mixture is about neutral, preferably said pH is 6 to 8, more preferably 6.8 to 7.5, and most preferably said pH is 7.2. In a very preferred embodiment said mixture comprises a phosphate buffer, preferably a sodium phosphate buffer, wherein further preferably the final concentration of said phosphate buffer in said mixture is 2 to 100 mM, more preferably 10 to 50 mM and most preferably about 20 mM.

In a further embodiment said mixture further comprises salt, wherein preferably said salt is a halogenide, preferably a chloride of an alkaline metal, more preferably said salt is potassium chloride or sodium chloride or a combination thereof, and most preferably said salt is sodium chloride. In a preferred embodiment the concentration of said salt or said combination of salts, preferably the concentration of said sodium chloride, in said mixture is 0 to 1 M, preferably 0 to 550 mM, more preferably 0 to 350 mM, still more preferably 50 to 350 mM, and most preferably 250 mM.

The capsid and/or virus-like particles of certain RNA bacteriophages, in particular of bacteriophage Qβ, bacteriophage AP205, and bacteriophage fr, are stabilized by intermolecular disulfide bonds between the protein subunits forming said capsid or virus-like particle. The addition of a reducing agent to said mixture keeps said disulfide bridges in a reduced state and, thus, supports the prevention of the self assembly of said coat protein. In a preferred embodiment said agent therefore further comprises a reducing agent, wherein said reducing agent is preferably selected from DTT (dithioerythol), β-mecaptoetanol, TCEP and other reducing agents generally known in the art. In a preferred embodiment said reducing agent is DTT, wherein preferably the concentration of said DTT in said mixture is 1 to 25 mM, preferably 2.5 mM. In a very preferred embodiment said RNA bacteriophage is bacteriophage Qβ, bacteriophage AP205, or bacteriophage fr, and said agent further comprises a reducing agent, wherein preferably said reducing agent is DTT, and wherein further preferably the concentration of said DTT in said mixture is 1 to 25 mM, preferably 2.5 mM. In a further preferred embodiment said coat protein comprises cystein residues capable of forming intermolecular disulfide bonds in said virus-like particle, and said agent further comprises a reducing agent, wherein preferably said reducing agent is DTT, and wherein further preferably the concentration of said DTT in said mixture is 1 to 25 mM, preferably 2.5 mM.

In a preferred embodiment said generating said mixture comprises adding (i) said coat protein; (ii) said agent capable of preventing the self-assembly of said coat protein; and (iii) said oligonucleotide to said mixture, wherein preferably said adding is performed in the given order, and wherein further preferably said mixture is mixed prior to said adding of said oligonucleotide.

In a further preferred embodiment said process further comprises the step of incubating said mixture prior to said removing of said agent, wherein preferably said incubating is performed for about 50 to 70, preferably about 60 min. In a further preferred embodiment incubating of said mixture is performed at 15 to 30° C., more preferably at 19 to 25° C., and most preferably at 22° C. In a further preferred embodiment said incubating of said mixture comprises stirring said mixture, wherein preferably said stirring is performed at about 50 to 200 rpm, most preferably at about 100 rpm. In a very preferred embodiment said incubating of said mixture is performed for about 60 min, and said incubating of said mixture comprises stirring said mixture, wherein preferably said stirring is performed at about 100 rpm.

In one embodiment said removing of said agent from said mixture is performed by a first buffer exchange with a first buffer, wherein preferably said first buffer exchange is performed by dialysis or by continuous flow filtration, preferably by continuous flow filtration. Said first buffer exchange is performed across a membrane comprising a molecular weight cut off which allows the retention of said coat protein and of the self assembled VLP. In a preferred embodiment said first buffer exchange is performed across a membrane, wherein said membrane comprises a molecular weight cut off of 1 to 50 kD, preferably of 5 to 30 kD, most preferably of 30 kD. In a very preferred embodiment said first buffer exchange is performed by continuous flow filtration across a membrane comprising a molecular weight cut off of 1 to 50 kD, preferably of 30 kD, wherein further preferably the volume of said first buffer is about 6 times the volume of said mixture. In a very preferred embodiment said membrane is Biomax-5 (PES) comprising 30 kD molecular weight cut off. In a very preferred embodiment said first buffer exchange is performed by continuous flow filtration across a membrane comprising a molecular weight cut off of 1 to 50 kD, preferably of 30 kD, wherein the permeate flow is adjusted to about $961/(m^2*h)$.

In a further preferred embodiment said first buffer comprises a salt, wherein preferably the salt composition of said first buffer is identical to the salt composition of said mixture. In a preferred embodiment said salt in said first buffer is a halogenide, preferably a chloride of an alkaline metal, more preferably said salt is potassium chloride or sodium chloride or a combination thereof, and most preferably said salt is sodium chloride. In a preferred embodiment the concentration of said salt or said combination of salts, preferably the concentration of said sodium chloride, in said first buffer is 0 to 1 M, preferably 0 to 550 mM, more preferably 0 to 350 mM, still more preferably 50 to 350 mM, and most preferably 250 mM. In a further preferred embodiment the pH of said first buffer is 6 to 8, more preferably 6.8 to 7.5, and most preferably said pH is 7.2. In a further preferred embodiment said first buffer comprises a phosphate buffer, preferably a sodium phosphate buffer, wherein further preferably the final concentration of said phosphate buffer in said first buffer is 2 to 100 mM, more preferably 10 to 50 mM and most preferably about 20 mM.

In order to stabilize said virus-like particle formed in the self assembly reaction, said virus-like particle is preferably contacted with an oxidizing agent capable of forming intermolecular disulfide bonds in said virus-like particle. Thus, in a preferred embodiment said process further comprises the step of contacting said virus-like particle with an oxidizing agent, wherein preferably said oxidizing agent is selected from the group consisting of (a) hydrogen peroxide, wherein preferably the concentration of said hydrogen peroxide is 0.25-50 mM, preferably 2 mM; (b) oxygen; (c) gluthathion; (d) ascorbate; (e) $Cu^{2+}$; and (f) $Fe^{3+}$. In a very preferred embodiment said RNA bacteriophage is bacteriophage Qβ, bacteriophage AP205, or bacteriophage fr, and said process further comprises the step of contacting said virus-like particle with an oxidizing agent, wherein preferably said oxidizing agent is selected from the group consisting of (a) hydrogen peroxide, wherein preferably the concentration of said hydrogen peroxide is 0.25-50 mM, preferably 2 mM; (b)

oxygen; (c) gluthathion; (d) $Cu^{2+}$; and (e) $Fe^{3+}$, and wherein most preferably said oxidizing agent is hydrogen peroxide, wherein further preferably the concentration of said hydrogen peroxide is 0.25-50 mM, preferably 2 mM. In a preferred embodiment said coat protein comprises cystein residues capable of forming intermolecular disulfide bonds in said virus-like particle, wherein preferably said coat protein is coat protein of bacteriophage Qβ, bacteriophage AP205 or bacteriophage fr, and said process further comprises the step of contacting said virus-like particle with an oxidizing agent, wherein preferably said oxidizing agent is selected from the group consisting of (a) hydrogen peroxide, wherein preferably the concentration of said hydrogen peroxide is 0.25-50 mM, preferably 2 mM; (b) oxygen; (c) gluthathion; (d) $Cu^{2+}$ and (e) $Fe^{3+}$, and wherein most preferably said oxidizing agent is hydrogen peroxide, wherein further preferably the concentration of said hydrogen peroxide is 0.25-50 mM, preferably 2 mM.

In a further preferred embodiment said process further comprises the step of purifying said virus-like particle, wherein preferably said purifying comprises a second buffer exchange with a second buffer, wherein further preferably said second buffer is a pharmaceutically acceptable buffer. In a preferred embodiment said second buffer exchange is performed with a second buffer, wherein preferably said second buffer exchange is performed by dialysis or by continuous flow filtration, preferably by continuous flow filtration. Said second buffer exchange is performed across a membrane comprising a molecular weight cut off which allows the retention of said virus-like particle, and which preferably allows the permeation of said coat protein and/or of said oligonucleotide. Thus, in a preferred embodiment said second buffer exchange is performed across a membrane comprising a molecular weight cut off of 100 to 1000 kD, preferably of 300 kD, wherein preferably said second buffer exchange is performed by continuous flow filtration. In a very preferred embodiment said membrane is PLCMK-300 comprising 300 kD molecular weight cut off. In a further very preferred embodiment said second buffer exchange is performed by continuous flow filtration across a membrane comprising a molecular weight cut off of 100 to 1000 kD, preferably of 300 kD, wherein preferably about 10 times the volume of said mixture is exchanged, and wherein further preferably the permeate flow is adjusted to about 100 l/(m²*h).

In a further embodiment said process comprises concentrating said virus-like particle, wherein preferably said concentrating is performed to a final concentration of said virus like particle in said composition of 1 to 5 mg protein/ml, preferably of about 2.5 mg protein/ml, wherein preferably said concentration is determined by Bradford protein assay, and wherein further preferably said virus-like particle is dissolved in said second buffer. In a very preferred embodiment said concentrating is performed across a membrane capable of retaining said virus-like particle, wherein preferably the molecular weight cut off of said membrane is 100 to 1000 kD, preferably about 300 kD, and wherein further preferably said concentrating is performed with a permeate flow across said membrane of less than 100 l/(h*m²), preferably about 30 l/(h*m²). Low flow rates during the concentration step prevent the precipitation of the product.

In a further preferred embodiment said process further comprises the step of sterile filtrating said virus-like particle, wherein preferably said virus-like particle is contained in said second buffer, wherein further preferably said sterile filtrating is performed across a membrane filter comprising 0.1 to 0.45 μm, preferably about 0.22 μm.

In a further preferred embodiment the processes according to the invention for producing a composition comprising (i) a virus-like particle, wherein said virus-like particle is a virus-like particle of an RNA bacteriophage, and (ii) an oligonucleotide, wherein said oligonucleotide is packaged into said virus-like particle, comprise a protein yield, wherein said protein yield is at least 50%, preferably at least 60%, more preferably at least 70%, still more preferably at least 75%, and most preferably at least 80%.

In a further preferred embodiment the processes according to the invention for producing a composition comprising (i) a virus-like particle, wherein said virus-like particle is a virus-like particle of an RNA bacteriophage, and (ii) an oligonucleotide, wherein said oligonucleotide is packaged into said virus-like particle, comprise an oligonucleotide yield, wherein said oligonucleotide yield is at least 50%, preferably at least 60%, more preferably at least 70%, still more preferably at least 75%, and most preferably at least 80%.

In a further preferred embodiment said composition comprising said virus-like particle comprises a purity of at least 80%, preferably at least 90%, more preferably at least 95%, still more preferably at least 98%, and most preferably at least 99%.

In a further preferred embodiment the processes according to the invention for producing a composition comprising (i) a virus-like particle, wherein said virus-like particle is a virus-like particle of an RNA bacteriophage, and (ii) an oligonucleotide, wherein said oligonucleotide is packaged into said virus-like particle, comprise an oligonucleotide yield, wherein said oligonucleotide yield is at least 50%, preferably at least 60%, more preferably at least 70%, still more preferably at least 75%, and most preferably at least 80%.

In a further preferred embodiment the processes according to the invention for producing a composition comprising (i) a virus-like particle, wherein said virus-like particle is a virus-like particle of an RNA bacteriophage, and (ii) an oligonucleotide, wherein said oligonucleotide is packaged into said virus-like particle, comprise a protein yield and an oligonucleotide yield, wherein said protein yield is at least 50%, preferably at least 60%, more preferably at least 70%, still more preferably at least 75%, and most preferably at least 80%.

In a further preferred embodiment said composition comprising said virus-like particle comprises 15 to 30 μg, preferably 20 to 25 μg, and most preferably about 20 μg of said oligonucleotide per 100 μg coat protein, wherein preferably said virus-like particle is a virus like particle of bacteriophage Qβ, and wherein further preferably said oligonucleotide is G10 (SEQ ID NO:8), wherein still further preferably said composition comprising said virus-like particle comprises a purity of at least 98%, preferably of at least 99%, wherein still further preferably the quantification of said coat protein is performed by Bradford protein assay, and wherein still further preferably the quantification of said oligonucleotide is performed essentially, preferably exactly as disclosed in Example 9.

The invention further relates to the use of a nucleotide composition obtainable by any one of the processes of the invention, in a process for producing a composition comprising (i) a virus-like particle, wherein said virus-like particle is a virus-like particle of an RNA bacteriophage, and (ii) an oligonucleotide, wherein said oligonucleotide is packaged into said virus-like particle, wherein preferably said process comprises the steps of (a) providing coat protein of said RNA bacteriophage; (b) providing said nucleotide composition; (c) generating a mixture, wherein said mixture comprises: (i) said coat protein; (ii) an agent capable of preventing the self-assembly of said coat protein; (iii) said oligonucleotide; (d) removing said agent from said mixture; and (e) allowing said coat protein to self assemble into a virus-like particle; wherein preferably said oligonucleotide contained in said nucleotide composition comprises a relative peak start time of 50 to 110%, wherein further preferably said RNA bacteriophage is Qβ, and wherein still further preferably said oligonucleotide is G10 (SEQ ID NO:8).

The invention further relates to the use of an oligonucleotide comprising a relative peak start time of 50 to 110% in a process for producing a composition comprising (i) a virus-like particle, wherein said virus-like particle is a virus-like particle of an RNA bacteriophage, and (ii) an oligonucleotide, wherein said oligonucleotide is packaged into said virus-like particle, wherein preferably said process comprises the steps of (a) providing coat protein of said RNA bacteriophage; (b) providing said oligonucleotide, (c) generating a mixture, wherein said mixture comprises: (i) said coat protein; (ii) an agent capable of preventing the self-assembly of said coat protein; (iii) said oligonucleotide; (d) removing said agent from said mixture; and (e) allowing said coat protein to self assemble into a virus-like particle; wherein preferably said RNA bacteriophage is Qβ, and wherein further preferably said oligonucleotide is G10 (SEQ ID NO:8).

The invention further relates to a composition obtainable by any one of the processes of the invention, said composition comprising (i) a virus-like particle, wherein said virus-like particle is a virus-like particle of an RNA bacteriophage, and (ii) an oligonucleotide, wherein said oligonucleotide is packaged into said virus-like particle, wherein preferably said RNA bacteriophage is Qβ, and wherein further preferably said oligonucleotide is G10 (SEQ ID NO:8), and wherein still further preferably the purity of said composition is at least 80%, preferably at least 90%, more preferably at least 95%, still more preferably at least 98% and most preferably at least 99%, and wherein still further preferably said composition comprising said virus-like particle comprises 15 to 30 µg, preferably 20 to 25 µg, and most preferably about 20 µg of said oligonucleotide per 100 µg coat protein.

The invention further relates to a composition obtainable by any one of the processes of the invention, said composition comprising (i) a virus-like particle, wherein said virus-like particle is a virus-like particle of an RNA bacteriophage, and (ii) an oligonucleotide, wherein said oligonucleotide is packaged into said virus-like particle, wherein preferably said RNA bacteriophage is Qβ, and wherein further preferably said oligonucleotide is G10 (SEQ ID NO:8), wherein still further preferably the purity of said composition is at least 80%, preferably at least 90%, more preferably at least 95%, still more preferably at least 98% and most preferably at least 99%, wherein said oligonucleotide in not accessible to DNAse hydrolysis.

EXAMPLES

Example 1

Disaggregation and Aggregation of Oligonucleotide G10 (SEQ ID NO:8)

Quantification of G10:
G10 was quantified by UV absorption at 260 nm corrected by the absorption at 340 nm, wherein 1 $A_{260\text{-}340}$ corresponds to a concentration of 27.8 µg/ml at 1 cm path length.

Disaggregation (10.0 ml scale, 260 µM G10, 25 mM NaOH, 50° C., 70 min):

45.91 mg G10 were weighed into a 15 ml tube. The powder was dissolved in 11.0 ml purified water (c=325.3 µM; determined by spectrometry). 8.0 ml of the oligonucleotide solution were mixed with 250 µl 1 M NaOH and 1.75 ml purified water in a 15 ml tube (260 µM G10, 25 mM NaOH). The mixture was disaggregated for 70 minutes at 50° C. in a water bath. After cooling the solution on ice, the pH was adjusted with 0.5 M HCl to pH 5.31; 540 µl 0.5 M HCl and 5 µl 1 M NaOH were added.

Aggregation (10.0 ml scale, 175 µM G10, 250 mM $Na^+$, 85° C., 9-24 min):
7.1 ml disaggregated G10 solution, 2.13 ml purified water and 770 µl 3 M NaCl were mixed in a 15 ml tube (175 µM oligo, 250 mM $Na^+$). The mixture was incubated for 9 minutes at 85° C. in a water bath. The solution was cooled down in an ice/water bath and stored on ice until use. Aggregated oligonucleotide solutions should be used within 3 hours after preparation.

Example 2

Disaggregation and Aggregation of Oligonucleotides G4-4

Disaggregation:
A solution of 260 µM oligonucleotide G4-4 (SEQ ID NO:2) and 25 mM NaOH in purified water was prepared. The solution was heated to 50° C. for 70 min and was then cooled down on ice, the pH of the solution was adjusted to a pH between 5 and 8 using 0.5 M HCl.

Aggregation:
The solution comprising the disaggregated G4-4 was diluted with purified water and 3 M NaCl to a final concentration of 230 µM G4-4 and 250 mM $Na^+$. The mixture is was heated to 80° C. using a heating ramp of 6.8° C./min for several minutes (2 to 70 min). After the incubation the mixture was cooled down to 0-2° C. with a temperature ramp of 6.8° C./min.

Analysis of the product by size exclusion HPLC (see Example 4) revealed that aggregated oligonucleotide was obtained. (relative peak start time: 88%).

Example 3

Disaggregation and Aggregation of Oligonucleotides

Disaggregation:
A solution of 260 µM oligonucleotide G5-5 (SEQ ID NO:3), G6-6 (SEQ ID NO:4), G7-7 (SEQ ID NO:5), G8-8 (SEQ ID NO:6), G9-9 (SEQ ID NO:7) and G11 (SEQ ID NO:9), respectively, and 25 mM NaOH in purified water is prepared. The solution is heated to 50° C. for 70 min and is then cooled down on ice, the pH of the solution is adjusted to a pH between 5 and 8 using 0.5 M HCl.

Aggregation:
The solution comprising the disaggregated oligonucleotide is diluted with purified water and 3 M NaCl to a final concentration of 230 µM oligonucleotide and 250 mM $Na^+$. The mixture is was heated to 80° C. using a heating ramp of 6.8° C./min for several minutes (2 to 70 min). After the incubation the mixture was cooled down to 0-2° C. with a temperature ramp of 6.8° C./min.

The product of the aggregation process is analyzed by size exclusion HPLC (see Example 4).

Example 4

Analysis of the Aggregation State of Oligonucleotide G10 by Size Exclusion HPLC The aggregation state of G10 was analyzed by analytical size exclusion HPLC using the following conditions:

| | |
|---|---|
| Column: | TSKgel 5000 PWXL 7.8 mm * 30.0 cm (Lot: 5PWX06GNMH3304, Art: 08023, Tosoh Bioscience) |
| Eluent: | PBS (150 mM NaCl in 20 mM sodium phosphate buffer, pH 7.2) |
| Injection volume: | 40.0 µl (preferably comprising a concentration of about 20 µM to about 500 µM) |
| Flow rate: | 0.8 ml/min |
| Gradient: | Isocratic |
| Run time: | 20 min |
| Wavelength: | 215, 260 and 280 nm, data evaluation at 260 nm |
| Column oven temp.: | 25° C. |
| Autosampler temp.: | 8° C. |

Capsid of bacteriophage Qβ was used as standard.

The peak start time X % of G10 relative to Qβ capsid (relative peak start time Qβ) was calculated as follows: X %=peak start time [min] of the oligonucleotide divided by the retention time of Qβ capsid standard [min]×100%, wherein the peak start time of the oligonucleotide was determined as the time when the elution of the oligonucleotide became detectable, and wherein the retention time of the Qβ capsid standard was determined as the time of the occurrence of the maximum peak of the standard. An Example of an elution profile of oligonucleotide G10 and capsid of bacteriophage Qβ as standard is depicted in FIG. 1. Based on the chromatograms depicted in FIG. 1 a relative peak start time of 88% calculated for the aggregated oligonucleotide.

Example 5

Comparison of the Relative Peak Start Times of Untreated, Disaggregated and Aggregated Oligonucleotide G10

The relative peak start time of disaggregated and aggregated G10 prepared essentially as described in Example 1 was determined and compared to the relative peak start time of untreated G10 as obtained from a commercial supplier. Disaggregated G10 showed a relative peak start time of 138% (136.9-140.3%; n=5). G10 preparations which have not undergone the disaggregation/aggregation treatment described in Example 1 show a relative peak start time in the same range as disaggregated G10. After disaggregation and aggregation, peak start time of G10 was found to be 88%.

Example 6

The Impact of the Disaggregation Step

Untreated oligonucleotide G10 and oligonucleotide G10 disaggregated as described in Example 1 was subjected to aggregation essentially as described in Example 1, wherein the following aggregation conditions were chosen: 175 µM G10, 250 mM $Na^+$ (by addition of 3 M NaCl), incubation at 85"C for 16 minutes, then cooling on ice. Both preparations were analyzed by size exclusion HPLC (see Example 4) using Qβ capsid and untreated G10 as standard. The resulting HPLC chromatograms are depicted in FIG. 2.

Figure 2:
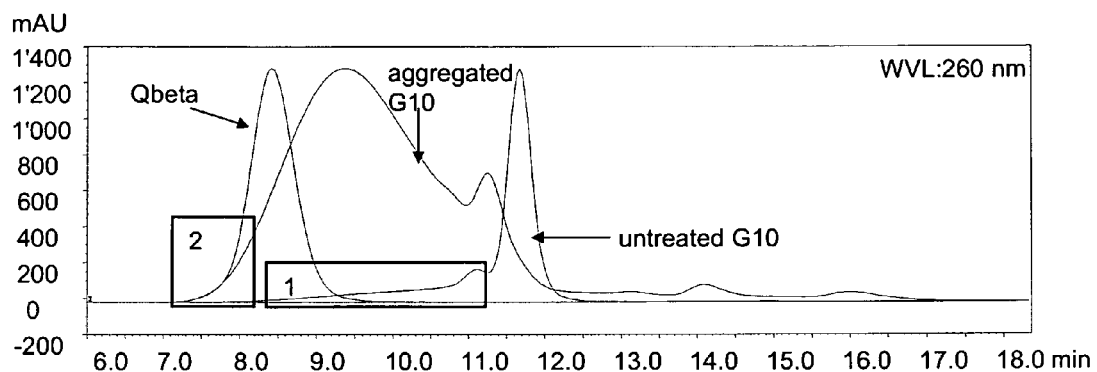
FIG. 2: Size exclusion HPLC chromatogram of untreated G10, aggregated oligonucleotide G10 and Qβ capsid standard. HPLC was performed as described in Example 4 (A) Aggregated G10 that was not subjected to a disaggregation treatment prior to aggregation showed an equivalent or higher apparent molecular weight than Qβ capsid (A, box 2). The relative peak start time was ca. 75%. (B) Aggregated G10 which prior to aggregation was subjected to a disaggregation treatment as described in Example 1 exhibited a lower apparent molecular weight than Qβ capsid (B, box 2). The relative peak start time was ca. 88%.
Figure 2:
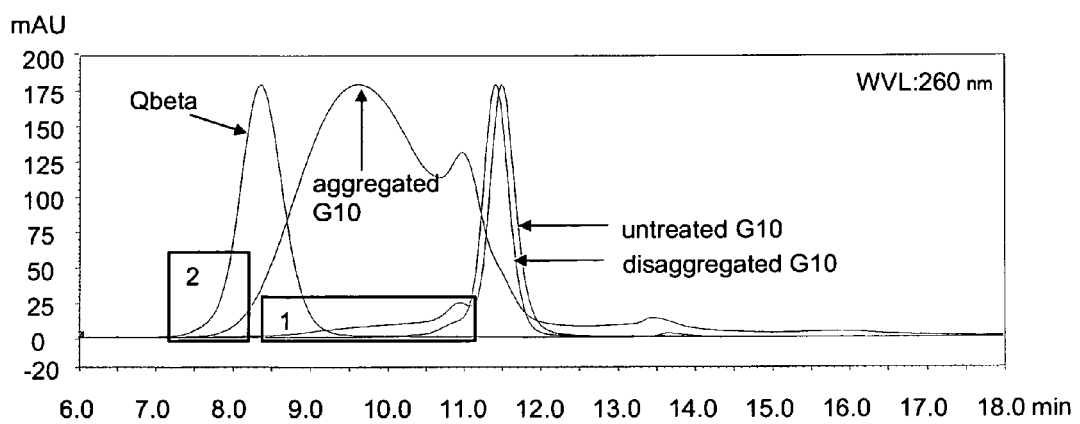

Untreated G10 contained aggregated G10 (see FIGS. 2A and 2 B, box 1). Aggregated G10 which was not disaggregated prior to aggregation showed an equivalent or higher apparent molecular weight than Qβ capsid (FIG. 2A, box 2). The relative peak start time was ca. 75%. Aggregated G10 which was disaggregated prior to aggregation exhibited a lower apparent molecular weight than Qβ capsid (FIG. 2B, box 2). The relative peak start time was ca. 88%.

Example 7

Figure 3:
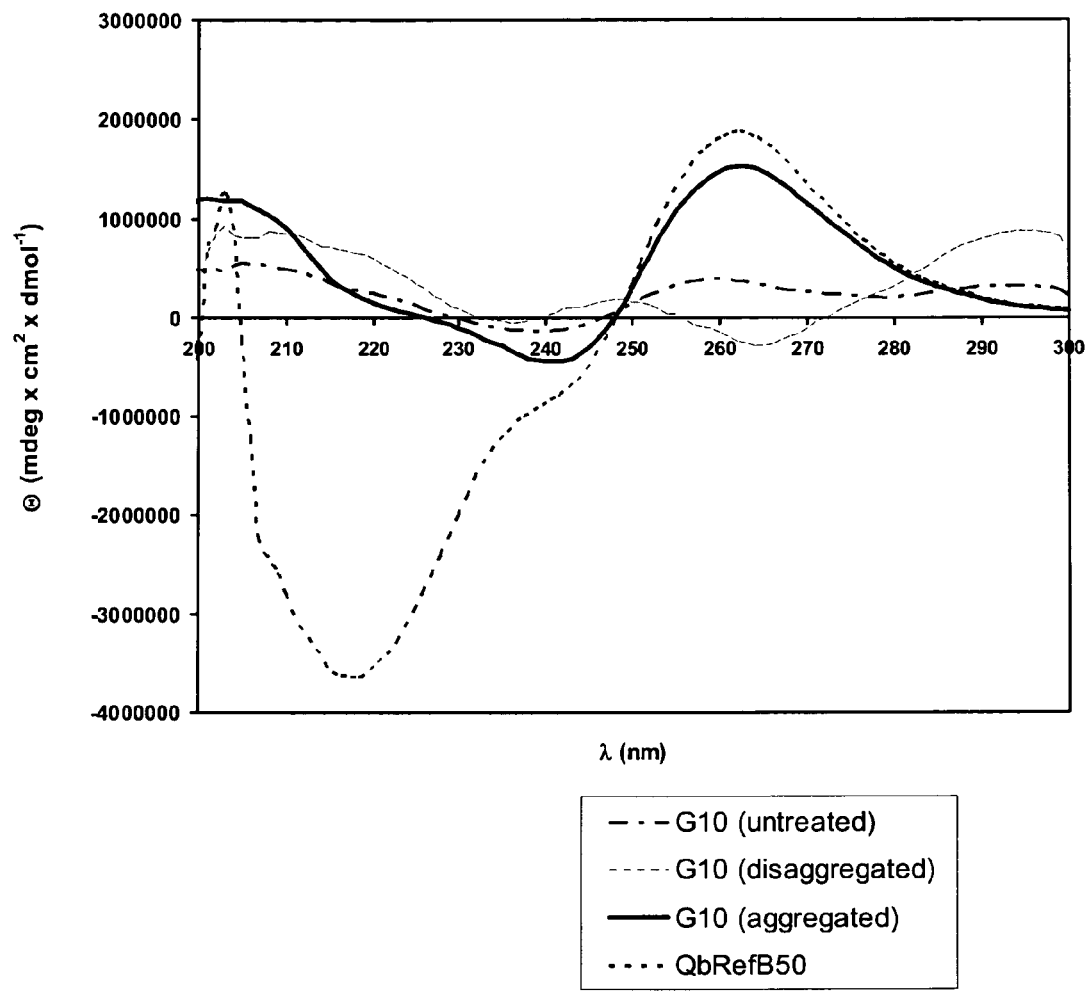
FIG. 3: CD spectra of untreated, disaggregated and aggregated G10 oligonucleotide and reassembled VLP packed with G10. Spectra were recorded using oligonucleotide concentrations of 22.5 µM and subsequently normalized. For normalization, ellipticities are calculated according to Θ=100×CD signal [mdeg]/L [cm]×c[mM].

Analysis of the Aggregation State of oligonucleotide G10 by Circular Dichroism CD spectra of untreated, disaggregated and aggregated G10 (prepared essentially as described in Example 1) as well as of Qβ capsid packaged with G10 (QbG10 obtained as described in Example 10) were recorded between 200 nm and 300 nm on a JASCO J-715 spectrophotometer. (FIG. 3). The spectrum of aggregated G10 is characterized by a strong positive band (high elliptic) with a maximum at 262 nm and a trough at 240 nm. These signals are reported to correspond to the typical spectrum of DNA tetraplexes with a parallel orientation of strands (Lu et al., Biochemistry 31, p. 2455, 1992). Importantly, the shape of the CD spectrum in the region of 250 nm-300 nm does not change in spectra of VLPs reassembled in the presence of aggregated G10. Thus, G10 does not seem to undergo a conformational change upon packaging. The slight increase of the amplitude at 262 nm possibly reflects the selective packing of aggregated G10 into Qβ capsids resulting in a higher proportion of tetraplexes after packaging compared to aggregated G10 which still contains a fraction of non-aggregated molecules. In contrast, the spectrum of untreated G10 is characterized by low ellipticities without defined maxima indicating a lack of defined secondary and tertiary structure elements. Low CD signals are also observed for disaggregated G10 even though the occurrence of a maximum at 295 nm and a minimum at 262 nm might reflect the presence of some antiparallel tetraplex conformers (P. Balagurumoorthy et al., Nucleic Acids Research 20, p. 4061, 1992).

Example 8

Packaging of Qβ VLPs with G10 by Disassembly/Reassembly

Disassembly of Qβ VLPs:

45 mg Qβ VLP (2.5 mg/ml, as determined by Bradford analysis) in PBS (20 mM Phosphate, 150 mM NaCl, pH 7.5), was reduced with 10 mM DTT for 15 min at RT under stirring conditions. Then, magnesium chloride was added to 0.7 M final concentration and the incubation was continued for 15 min at RT under stirring conditions, leading to precipitation of the encapsulated host cell RNA and concomitant disintegration of the VLPs. The solution was centrifuged 10 min at 4000 rpm at 4° C. (Eppendorf 5810 R, in fixed angle rotor A-4-62 used in all following steps) in order to remove the precipitated RNA from the solution. The supernatant, containing the released, dimeric Qβ coat protein, was used for the chromatographic purification steps.

Purification of Qβ Coat Protein by Cation Exchange Chromatography and Size Exclusion Chromatography:

The supernatant of the disassembly reaction, containing dimeric coat protein, host cell proteins and residual host cell RNA, was loaded onto a SP-Sepharose FF column (xk16/20, 6 ml, Amersham Bioscience). The column was equilibrated with 20 mM sodium phosphate buffer pH 7 and the sample was diluted 1:15 in water to adjust a conductivity below 10 mS/cm in order to achieve proper binding of the coat protein to the column. The elution of the bound coat protein was accomplished by a step gradient to 20 mM sodium phosphate/500 mM sodium chloride and the protein was collected in a fraction volume of approx. 25 ml. The chromatography was carried out at RT with a flow rate of 5 ml/min during all steps and the absorbance was monitored at 260 nm and 280° nm. In a second step, the isolated Qβ coat protein (the eluted fraction from the cation exchange column) was loaded onto a Sephacryl S-100 HR column (xk26/60, 320 ml, Amersham Bioscience) equilibrated with 20 mM sodium phosphate/250 mM sodium chloride; pH 7.2. The chromatography was carried out at RT with a flow rate of 2.5 ml/min and the absorbance was monitored at 260 nm and 280 nm. Fractions of 5 ml were collected.

Figure 4:
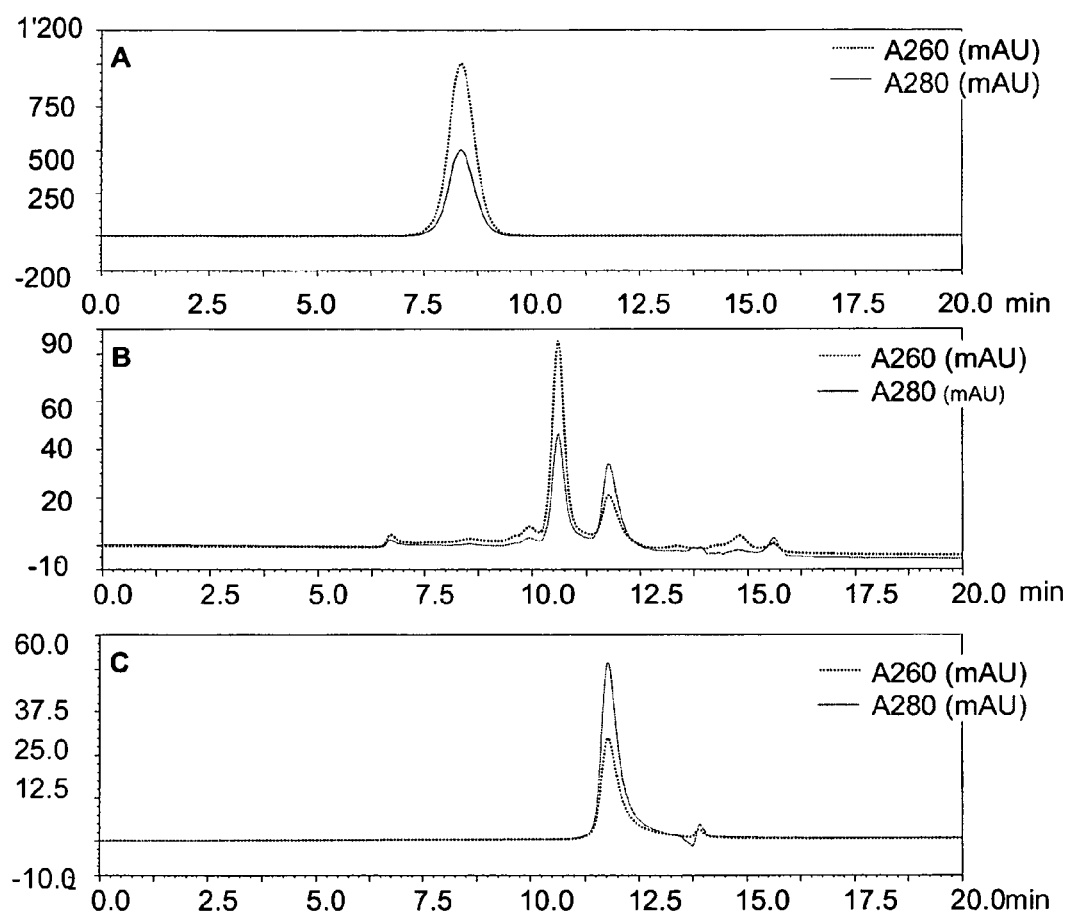
FIG. 4: Characterization of purified Qβ coat protein by analytical size exclusion chromatography. (A) sample of purified Qβ VLP. The observed peak (ratio A260/A280=2) is dominated by the RNA core of the VLP, because the absorption coefficient of RNA at 260 nm is approx. 100 fold higher than the absorption coefficient of the coat protein. (B) sample of the supernatant of the disassembly reaction. Released coat protein is indicated by the presence of the protein-like peak at approx. 12 min. Furthermore several species of non-precipitated RNA molecules are present in the range 6.8 to 11 min. (C) sample of purified Qβ coat protein. Analysis was performed in PBS on column TSK G5000PWx1 (Tosoh Bioscience).

Characterization of Purified Qβ Coat Protein by Analytical Size Exclusion Chromatography:

A sample of purified Qβ coat protein was analyzed by analytical size exclusion chromatography (FIG. 1C) and compared to i) intact Qβ VLP (FIG. 4A), which had been purified from *E. coli* lysate and which was used as source material for the purification procedure, and ii) to the supernatant of the disassembly reaction (FIG. 4B). Efficient separation of RNA molecules from the coat protein is indicated by the absence of any RNA-like peak (typical ratio of A280/A260=0.5) in FIG. 4C and the presence of a unique protein-like peak (typical ratio of A280/A260=1.7).

Assembly of QβG10 by Diafiltration:

Purified coat protein (in 20 mM sodium phosphate pH 7.2, 250 mM NaCl) was mixed with water and stock solutions of urea, NaCl, DTT and aggregated G10 oligonucleotide (prepared essentially as described in Example 1). The volume of the mixture was 50 ml and the final concentrations of the components were 1 mg/ml coat protein, 1.0 M urea, 250 mM NaCl, 2.5 mM DTT and 0.24 mg/ml G10. The solution was then diafiltrated at room temperature against 300 ml of 20 mM sodium phosphate 250 mM NaCl pH 7.2, using a 30 kDa cut off cartridge (Pellicon X L, Millipore) and a cross flow rate of 10 ml/min and a permeate flow rate of 2.5 ml/min. $H_2O_2$ was added to 7 mM final concentration and the solution incubated for 1 h at RT in order to induce the formation of disulfide bonds. The solution was then diafiltrated against 500 ml of 20 mM sodium phosphate 150 mM NaCl pH 7.2, using a 300 kDa cut off cartridge (Pellicon X L, Millipore) and a cross flow rate of 10 ml/min and a permeate flow rate of 2.5 ml/min, in order to remove excess of $H_2O_2$ and non-packaged G10 oligonucleotides from the assembled QβG10 product.

Example 9

Figure 5:
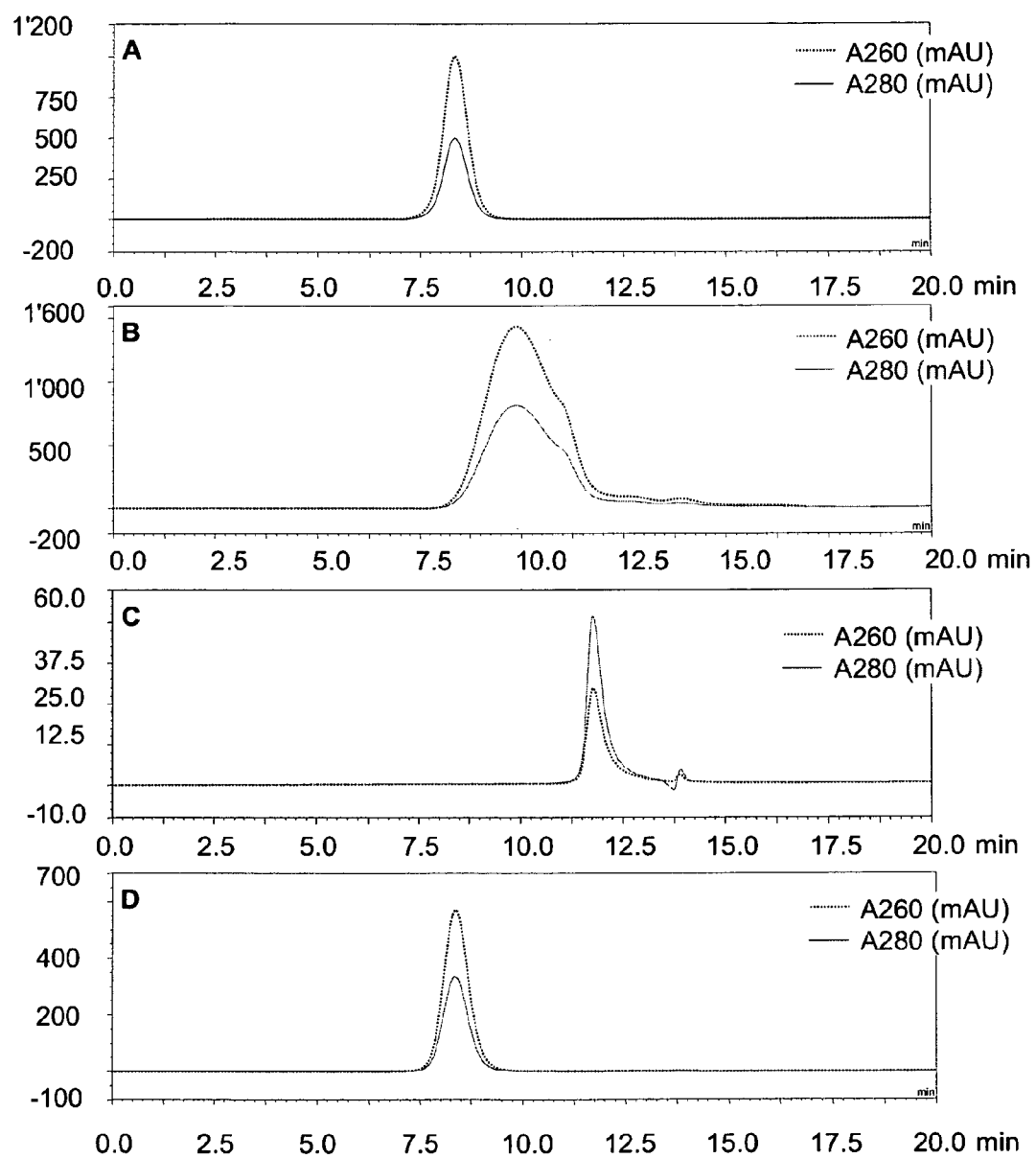
FIG. 5: Analytical size exclusion chromatography of (A) native Qβ VLP, (D) QβG10 VLP and the packaging components (B) oligo nucleotide G10 and (C) Qβ coat protein. The observed peak for QβG10 VLP (D) (ratio A260/A280=1.74) is dominated by the G10 core of the VLP, because the absorption coefficient of G10 at 260 nm is approx. 130 fold higher than the absorption coefficient of the coat protein. Analysis was performed in PBS on column TSK G5000PWx1 (Tosoh Bioscience).

Analysis of QβG10 Packaging Product and Determination of Yield of the Packaging Process Characterization of Packaged 013G10 VLP by Analytical Size Exclusion Chromatography:

A sample of packaged QβG10 VLP was analyzed by analytical size exclusion chromatography (FIG. 5) and compared to intact Qβ VLP, which had been purified from *E. coli* lysate. Said analytical size exclusion chromatography was performed using the following parameters:

| Column: | Bio-Sil SEC 250, 7.8 × 300 mm, Cat. No. 125-0062 |
|---|---|
| Eluent: | 50 mM Sodiumphospate pH 6.5, 150 mM NaCl |
| Gradient: | Isocratic |
| Column temperature: | 25° C. |
| Autosampler temperature: | 8° C. |
| Flow rate: | 1.0 ml/min |
| Sample concentration: | 1.0 mg/ml protein |
| Injection volume: | 40 μl |
| Evaluation wavelength: | 280 nm |
| Bandwith: | 4 nm |
| Run time: | 20 min |

Sample Preparation:
The sample was diluted to 1.0 mg/ml using eluent, the sample was vortexed shortly and centrifuged at 16'000 g for 10 minutes at 4° C.

The presence of correctly assembled VLP in the product was confirmed by a peak migrating at identical retention time as the peak representing native Qβ VLP. The observed peak for QβG10 VLP (FIG. 5D) is dominated by the nucleic acid content of the VLP, because the absorption coefficient nucleic acids at 260 nm is more than 100-fold higher than the absorption coefficient of the coat protein. The ratio A260/A280 of purified QβG10 VLP was found to be 1.70 (1.65-1.76; n=5), which is characteristic for G10 (A260/A280=1.74), wherein the A260/A280 ratio of Qβ VLP was found to be 1.87 (1.85-1.90; n=10) which is characteristic for RNA.

Figure 6:
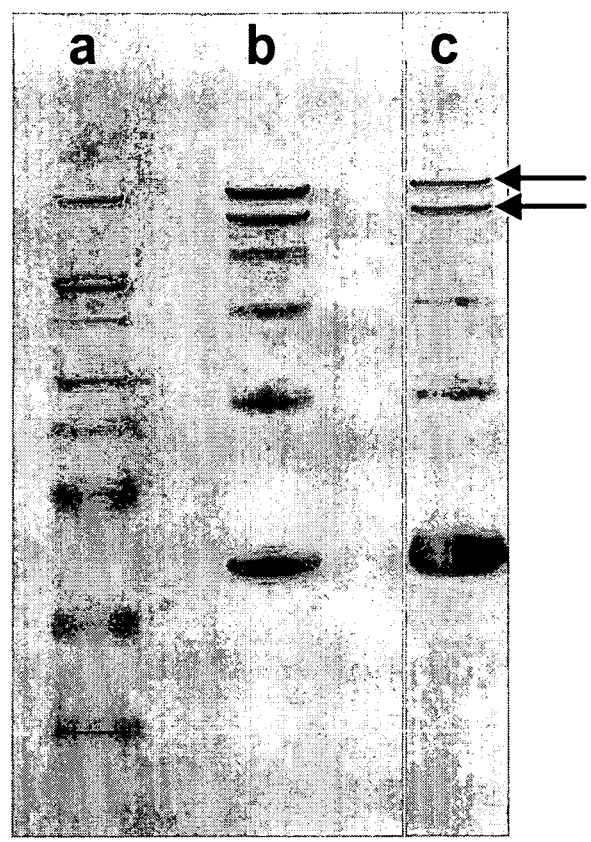
FIG. 6: Non-reducing SDS-PAGE analysis of native Qβ VLP and in vitro assembled QβG10. The position of the coat protein pentamers and hexamers is indicated ((a) molecular weight marker, (b) QβVLP, (c) Qβ G10).

Characterization of Packaged QβG10 VLP by SDS-PAGE Analysis:

A sample of packaged Qβ G10 was analyzed by non-reducing SDS-PAGE (FIG. 6) and compared to intact Qβ VLP, which had been purified from *E. coli* lysate. The presence of correctly assembled VLP in the product was confirmed by the formation of bands of disulfide-linked pentameric and hexameric forms of the coat protein, similar to the intact Qβ VLPs, indicating the correct structural arrangement of the coat protein units in the in vitro assembled Qβ G10 VLP.

Quantification of Packaged Oligonucleotide G10:

Samples of QβG10 VLP (0.25 mg/ml in PBS) were treated by 0.1 mM TCEP (Tris(2-chloroethyl)phosphate) (15 min at RT) in order to reduce the disulfide bonds. NaCl was added to the reduced samples (1 M final concentration) and the mixtures were incubated for 15 min at 60° C. in order to precipitate the protein component. After centrifugation, the resulting supernatants were incubated for 5 min at 95° C., cooled on ice for 1 min and then the A260 value was measured. The concentration of oligonucleotide G10 in the supernatants was calculated according to the formula:

$$c(G10)(mg/ml) = A_{260} \times 1.12 \times 9600/344580, \text{ where:}$$

1.12=correction factor for the salt content in the sample
9600=molecular mass of oligonucleotide G10
344580=specific molar absorption coefficient of oligonucleotide G10.

Typically, the amount of packaged oligonucleotide G10 was 0.2 mg per mg of Qβ coat protein.

G10 Content of QβG10 VLP and Yield Calculation for the Packaging Reaction:

Aggregated G10 was packaged into Qβ VLP by assembly/reassembly of the VLP as described in Example 8. 953 mg G10 oligonucleotide were introduced for reassembly with 4000 mg purified Qβ dimer. The reaction yielded QβG10 comprising 20 μg G10 oligonucleotide per 100 μg protein (protein content determined by Bradford analysis or HPLC). The G10 yield of the packaging reaction was 63% at a protein yield of 75%.

Example 10

Assembly of QβG10 by diafiltration and Determination of Yield

Purified Qβ coat protein was obtained essentially as described in Example 8. Coat protein in 20 mM sodium phosphate pH 7.2, 250 mM NaCl was mixed with water and stock solutions of urea, NaCl, DTT and aggregated G10 oligonucleotide (prepared essentially as described in Example 1; relative peak start time of disaggregated G10 was 135%, relative peak start time of aggregated G10 was 88%). The volume of the mixture was 1.6 L and the final concentrations of the components were 2.5 mg/ml coat protein, 1.0 M urea, 250 mM NaCl, 2.5 mM DTT and 0.6 mg/ml G10. The solution was then diafiltrated at room temperature against 9.6 L of 20 mM sodium phosphate 250 mM NaCl pH 7.2, using a 30 kDa cut off cartridge (Pellicon Mini2, 0.1 m² filter area, Millipore) and a cross flow rate of 384 L/(h*m²) and a permeate flow rate of 96 L/(h*m²). $H_2O_2$ was added to 2 mM final concentration and the solution incubated for 1 h at RT in order to induce the formation of disulfide bonds. The solution was then diafiltrated against 16 L of 20 mM sodium phosphate 150 mM NaCl pH 7.2, using a 300 kDa cut off cartridge (Pellicon Mini 2, 0.1 m² filter area, Millipore) and a cross flow rate of 300 l/(h*m²) and a permeate flow rate of 100 l/(h*m²), in order to remove excess of $H_2O_2$ and non-packaged G10 oligonucleotides from the assembled QβG10 product. The product was concentrated to 2.5 mg/ml by tangential flow filtration and filtered through a 0.22 μm filter. The major process steps are summarized in Table 1.

TABLE 1

Summary of the process steps for assembly and purification of QβG10.

| Process Step | Parameters | | Output of the Process Step |
|---|---|---|---|
| Disaggregation of G10 | G10 concentration: | 260 μM | relative peak start time of G10: 138% |
| | NaOH concentration: | 25 mM | |
| | Temperature: | 50° C. | |
| | Heating time: | 70 minutes | |
| | Scale: 1.1 g G10, V = 440 ml (in 10 ml Aliquots) | | |
| Neutralization of the disaggregated G10 solution | Used Acid: | 0.5 M H3PO4 | pH 7.2 |
| Reaggregation of the G10 solution | G10 concentration: | 175 μM | relative peak start time of G10: 88% |
| | Na⁺ concentration: | 250 mM | |
| | Temperature: | 85° C. | |
| | Heating time: | 10 minutes | |
| | Scale: 1.1 g G10, V = 654 ml (in 10 ml Aliquots) | | |
| Thawing of the starting material Preparation of the reassembly mixture. | Temperature: | 22° C. | Qbeta dimer solution |
| | Dimer concentration: | 2.5 mg/ml | Solution for diafiltration 1 |
| | Urea concentration: | 1 M | |
| | DTT concentration: | 2.5 mM | |
| | G10 concentration: | 62.5 μM | |
| | Mixing time: | 60 ± 10 minutes | |
| | Temperature: | 22 ± 3° C. | |
| | Scale: 4 g Qβ Dimer; V = 1.6 l | | |
| Continuous diafiltration 1 | Membrane: | 30 kDa MWCO | The Qbeta dimer forms VLPs around the G10 core material due to removal of urea and DTT. |
| | Area: | 0.1 m² | |
| | Diafiltration volumes: | 6 (9.6 L permeate collected) | |
| | Buffer: | NaP250 pH 7.2 | |
| | Target duration: | 60 minutes | |
| | Temperature: | 22° C. | |
| | Flux: | 96 l/(h*m²) | |
| | V = 1.6 l | | |
| Oxidation with hydrogen peroxide | H₂O₂ concentration: | 2 mM | Formation of disulfide bridges and therefore stabilization of the VLP |
| | Temperature: | 22° C. | |
| | Reaction time: | 60 ± 10 minutes | |
| | V = 1.6 l | | |
| Continuous Diafiltration 2 | Membrane: | 300 kDa MWCO | Removal of residual hydrogen peroxide and residual, unpackaged G10. |
| | Area: | 0.1 m² | |
| | Diafiltration volumes: | 10 (16 L) | |
| | Buffer: | pharmaceutically acceptable buffer | |
| | Temperature: | 22 ± 3° C. | |
| | Flux: | 100 l/(h*m²) | |
| | V = 1.6 l | | |
| Concentration of QbG10 | Membrane: | 300 kDa MWCO | Concentration = 2.5 mg/ml |
| | Area: | 0.1 m² | |
| | Temperature: | 22 ± 3° C. | |
| | Permeate Flow: | <100 l/(h*m²) | |
| | V = 1.2 l | | |
| Filtration of QbG10 | 0.22 μm PES membrane filter | | Bioburden reduction |

The purity of the product was analyzed by size exclusion chromatography was found to be 99.28%, i.e. the QbG10 peak amounted to 99.28% of the entire peak area in a chromatography run as described in Example 4. Protein yield and oligonucleotide yield were determined as described in Example 8. The protein yield across the entire process was 75%. The oligonucleotide yield across the entire process was 75%.

Example 11

Impact of the Aggregation State of G10 on the Assembly Process

When G10 with a relative peak start time of 139% was used in the assembly process as described in Example 8, only negligible amounts of GbG10 were formed and no VLP product could be isolated.

Example 12

Packaging of AP205 and GA355 VLPs with G10 by Disassembly/Reassembly

Disassembly:
50-100 mg of AP205 or GA355 VLPs (as determined by Bradford analysis) in buffer A (5 mM NaPO$_4$ pH 6.8, 100 mM NaCl, 2 mM MgCl$_2$) were incubated at 30° C. for 16 hours with RNAse A (Sigma) and Benzonase (Novagen) at 1 mg/ml and 5 U/ml, respectively. In the case of AP205 VLP deoxidation of the internal disulfide bridges was performed preceding the addition of RNAse A and Benzonase by addition of 20 mM DTT followed by a 30 min incubation at 37° C. After addition of 1 M NaCl precipitation of the viral coat proteins was induced by 15 min incubation at 70° C. Precipitated coat proteins were sedimented by centrifugation for 10 min, 27,000 g at 4° C. The supernatant containing RNAse A, Benzonase and degraded nucleic acids was discarded. Pellets were resuspended in buffer B (20 mM NaPO$_4$ pH 7.2, 6 M urea) and incubated for 10 min at room temperature.

Purification of Coat Proteins by Cation Exchange Chromatography:
The solutions were clarified by centrifugation for 10 min, 27,000 g at 4° C. A negligible pellet was discarded. And the supernatant containing the disassembled coat proteins were applied on a SP Sepharose™ FF column (16/20, Amersham Biosciences) equilibrated with buffer B (20 mM NaPO$_4$ pH 7.2, 6 M urea). The flow through was discarded. After an extensive wash with buffer B (15 CV) the column was adjusted with a linear gradient from buffer B to buffer C (20 mM NaPO$_4$ pH 7.2, 1 M urea) with a gradient length of 37.5 CV. During the loading, wash and elution the absorbance at 254 nm and 280 nm was monitored. Coat proteins were eluted as one fraction with buffer D (20 mM NaPO$_4$ pH 6.5, 1 M urea, 300 mM NaCl) and analyzed by LDS-PAGE followed by Coomassie staining Eluted protein fractions were stored at 4° C. as "disassembled coat protein". Protein concentrations were determined by Bradford analysis.

Reassembly:
Purified AP205 or GA355 coat protein was used in a five fold excess (w/w) to G10 oligonucleotide. The coat proteins were mixed with the G10 oligonucleotide in a reassembly buffer containing 1 M urea and 2.5 mM DTT and incubated for one hour at room temperature. After incubation the reassembly mix was dialyzed for 24 hours against 5 liter PBS. The resulting suspension was centrifuged for 10 min, 27,000 g at 4° C. A negligible sediment was discarded. The supernatant contained the reassembled and packaged VLPs. Protein concentration was determined by Bradford analysis and the reassembled and packaged VLPs were concentrated with centrifugal filter devices (Amicon Ultra 15, 10K MWCO).

Purification of Reassembled and Packaged VLPs:
Up to 25 mg total protein was loaded onto a Sepharose™ CL-4B (26/60, Amersham Biosciences) equilibrated with PBS. Size exclusion chromatography was performed with equilibration buffer at room temperature with a flow rate of 1.25 ml/min. During the elution absorbance at 254 nm and 260 nm was monitored. Two peaks were isolated. A major high molecular weight peak preceded a small peak of lower apparent molecular weight. The major peak revealed a apparent molecular weight consistent to purified VLPs as shown by SE-HPLC. Analysis of AP205 or GA355 VLPs packaged with G10 oligonucleotide is performed essentially as shown in Example 16 of WO03/024481 (p. 131 ff).

Example 13

Packaging of FR VLPs with G10 by Disassembly/Reassembly

Disassembly:
50-100 mg of FR VLPs (as determined by Bradford analysis) in buffer A (5 mM NaPO$_4$ pH 6.8, 100 mM NaCl, 2 mM MgCl$_2$) are incubated at 30° C. for 16 hours with RNAse A (Sigma) and Benzonase (Novagen) at 1 mg/ml and 5 U/ml, respectively. After addition of 1 M NaCl precipitation of the FR coat proteins is induced by a 15 min incubation at 70° C. Precipitated coat proteins are sedimented by centrifugation for 10 min, 27,000 g at 4° C. The supernatant containing RNAse A. Benzonase and degraded nucleic acids are discarded. The pellet is resuspended in buffer B (20 mM NaPO$_4$ pH 7.2, 6 M urea) and incubated for 10 min at room temperature.

Purification of FR Coat Proteins by Cation Exchange Chromatography:
The solution is clarified by centrifugation for 10 min, 27,000 g at 4° C. A negligible pellet is discarded and the supernatant containing the disassembled coat proteins is applied on a SP Sepharose™ FF column (16/20, Amersham Biosciences) equilibrated with buffer B. The flow through is discarded. After an extensive wash with buffer B (15 CV) the column is adjusted with a linear gradient from buffer B to buffer C (20 mM NaPO$_4$ pH 7.2, 1 M urea) with a gradient length of 37.5 CV. During the loading, wash and elution the absorbance at 254 nm and 280 nm is monitored. FR coat proteins are eluted as one fraction with buffer D (20 mM NaPO$_4$ pH 6.5, 1 M urea, 300 mM NaCl) and analyzed by LDS-PAGE followed by Coomassie staining. The eluted protein fractions is stored at 4° C. as "disassembled coat protein". Protein concentration is determined by Bradford analysis.

Reassembly:
Purified FR coat protein is used in a five fold excess (w/w) to G10 oligonucleotide. The FR coat proteins are mixed with the G10 oligonucleotide in a reassembly buffer containing 1 M urea and 2.5 mM DTT and incubated for one hour at room temperature. After incubation the reassembly mix is dialyzed for 24 hours against 5 liter PBS. The resulting suspension is centrifuged for 10 min, 27,000 g at 4° C. A negligible sediment is discarded. The supernatant contains the reassembled and packaged FR VLPs. Protein concentration is determined by Bradford analysis and the reassembled and packaged FR VLPs are concentrated with centrifugal filter devices (Amicon Ultra 15, 10K MWCO).

Purification of Reassembled and Packaged FR VLPs:

Up to 25 mg total protein is loaded onto a Sepharose™ CL-4B (26/60, Amersham Biosciences) equilibrated with PBS. Size exclusion chromatography is performed with equilibration buffer at room temperature with a flow rate of 1.25 ml/min. During the elution absorbance at 254 nm and 260 nm is monitored. Two peaks are isolated. A major high molecular weight peak precedes a small peak of lower apparent molecular weight. The major peak reveals a apparent molecular weight consistent to purified FR VLPs as shown by SE-HPLC. Analysis of FR VLPs packaged with G10 oligonucleotide is performed essentially as shown in Example 16 of WO 03/024481 (p. 131 ff).

Example 14

Assembly of QβG8 by Diafiltration and Determination of Yield

Purified Qβ coat protein is obtained essentially as described in Example 8. Coat protein in 20 mM sodium phosphate pH 7.2, 250 mM NaCl is mixed with water and stock solutions of urea, NaCl, DTT and aggregated G8 oligonucleotide (prepared essentially as described in Example 3; relative peak start time of disaggregated G8 is 113%, relative peak start time of aggregated G8 is 88%). The volume of the mixture is 1.6 L and the final concentrations of the components are 1 mg/ml coat protein, 1.0 M urea, 250 mM NaCl, 2.5 mM DTT and 0.24 mg/ml G8. The solution is then diafiltrated at room temperature against 9.6 L of 20 mM sodium phosphate 250 mM NaCl pH 7.2, using a 30 kDa cut off cartridge (Pellicon Mini2, 0.1 $m^2$ filter area, Millipore) and a cross flow rate of 384 L/(h*$m^2$) and a permeate flow rate of 96 L/(h*$m^2$). $H_2O_2$ is added to 2 mM final concentration and the solution is incubated for 1 h at RT in order to induce the formation of disulfide bonds. The solution is then diafiltrated against 16 L of 20 mM sodium phosphate 150 mM NaCl pH 7.2, using a 300 kDa cut off cartridge (Pellicon Mini 2, 0.1 $m^2$ filter area, Millipore) and a cross flow rate of 300 l/(h*$m^2$) and a permeate flow rate of 100 l/(h*$m^2$), in order to remove excess of $H_2O_2$ and non-packaged G8 oligonucleotides from the assembled QβG8 product. The product is concentrated to 2.5 mg/ml by tangential flow filtration and filtered through a 0.22 μm filter.

The invention claimed is:

1. A process for producing an nucleotide composition comprising aggregated oligonucleotides, said process comprising the steps of:
   (a) providing at least two oligonucleotides in solution I, wherein said oligonucleotides comprise at their 5' end at least 3 and at most 15 guanosine entities and at their 3' end at least 3 and at most 15 guanosine entities, wherein each oligonucleotide of said oligonucleotides comprise 20 to 40 nucleotides, and wherein said solution I comprises a pH of 10 to 13;
   (b) disaggregating said oligonucleotides, wherein said disaggregating comprises the steps of
      (i) adjusting the temperature of solution I to temperature I, wherein said temperature I is 20 to 70° C.;
      (ii) incubating said oligonucleotides in said solution I at said temperature I, wherein said incubating is performed until said oligonucleotides comprise a relative peak start time above 110%, and wherein said relative peak start time is determined in size exclusion HPLC with the capsid of an RNA bacteriophage as the standard; and
      (iii) adjusting the temperature of said solution I to temperature II, wherein said temperature II is 0 to 10° C.;
   (c) adjusting the pH of said solution I to 5 to 8; and
   (d) aggregating said oligonucleotides, wherein said aggregating comprises the steps of:
      (i) providing said oligonucleotides in said solution I and generating a solution II, wherein said solution II further comprises at least 20 mM of a cation, wherein said cation is selected from the group consisting of $Na^+$, $NH_4^+$, $Li^+$, $Ca^{2+}$, and $Mg^{2+}$;
      (ii) adjusting the temperature of solution II to temperature III, wherein said temperature III is 50 to 99° C.;
      (iii) incubating said oligonucleotides in solution II at temperature III, wherein said incubating is performed until said oligonucleotides comprise a relative peak start time of 80 to 110%, wherein said relative peak start time is determined in size exclusion HPLC with the capsid of an RNA bacteriophage as the standard; and
      (iv) adjusting the temperature of solution II to temperature IV, wherein said temperature IV is 0 to 10° C.

2. The process of claim 1, wherein said temperature I is 45 to 70° C.

3. The process of claim 1, wherein said adjusting of the temperature of said solution I to temperature II is performed with a temperature ramp of at least 3.6° C./min.

4. The process of claim 1, wherein said solution I comprises potassium hydroxide or sodium hydroxide.

5. The process of claim 1, wherein said adjusting of the pH of said solution I is performed by the addition of phosphoric acid, and wherein said adjusting of the pH of said solution I is performed until said pH is 6 to 7.

6. The process of claim 1, wherein said cation is $Na^+$ or $K^+$, and wherein said solution II comprises 200 to 275 mM of said cation.

7. The process of claim 1, wherein the concentration of said oligonucleotides in said solution I is 50 µM to 2 mM.

8. The process of claim 1, wherein the concentration of said oligonucleotides in said solution II is 50 µM to 2 mM.

9. The process of claim 1, wherein said incubating of said oligonucleotides in solution II at temperature III is performed until said oligonucleotides comprise a relative peak start time of 80 to 95%, and wherein said relative peak start time is determined in size exclusion HPLC with the capsid of an RNA bacteriophage as the standard.

10. The process of claim 1, wherein said oligonucleotides comprise a nucleic acid sequence selected from the group consisting of:

```
(a) "G4-4"
GGGGGACGATCGTCGGGG;              (SEQ ID NO: 2)

(b) "G5-5"
GGGGGGACGATCGTCGGGGG;            (SEQ ID NO: 3)

(c) "G6-6"
GGGGGGGACGATCGTCGGGGGG;          (SEQ ID NO: 4)

(d) "G7-7"
GGGGGGGGACGATCGTCGGGGGGG;        (SEQ ID NO: 5)

(e) "G8-8"
GGGGGGGGGACGATCGTCGGGGGGGG;      (SEQ ID NO: 6)

(f) "G9-9"
GGGGGGGGGGACGATCGTCGGGGGGGGG;    (SEQ ID NO: 7)

(g) "G10"
GGGGGGGGGGGACGATCGTCGGGGGGGGGG;  (SEQ ID NO: 8)

(h) "G11"
GGGGGGGGGGGGACGATCGTCGGGGGGGGGGG. (SEQ ID NO: 9)
```

11. The process of claim 1, wherein said oligonucleotides comprise the nucleic acid sequence "G10" GGGGGGGGGG GACGATCGTC GGGGGGGGGG (SEQ ID NO:8).

12. The process of claim 1, wherein said adjusting the temperature of solution II to temperature IV is performed with a temperature ramp of at least 3.6° C./min.

13. The process of claim 1, wherein said oligonucleotides comprise a palindromic sequence, wherein said palindromic sequence is GACCATCGTC (SEQ ID NO:1).

14. The process of claim 1, wherein said relative peak start time is determined in size exclusion HPLC with the capsid of an RNA bacteriophage Qβ as the standard.

15. The process of claim 9, wherein said relative peak start time is determined in size exclusion HPLC with the capsid of an RNA bacteriophage Qβ as the standard.

16. The process of claim 1, wherein said temperature I is room temperature.

17. The process of claim 1, wherein said temperature I is about 50° C.

18. The process of claim 1, wherein said temperature II is 0 to 2° C.

19. The process of claim 1, wherein said temperature IV is 0 to 2° C.

20. The process of claim 1, wherein said oligonucleotides consist of the nucleic acid sequence "G10" GGGGGGGGGG GACGATCGTC GGGGGGGGGG (SEQ ID NO:8).

* * * * *

SEQUENCE LISTING

```
<160> NUMBER OF SEQ ID NOS: 23

<210> SEQ ID NO 1
<211> LENGTH: 10
<212> TYPE: DNA
<213> ORGANISM: Artificial Sequence
<220> FEATURE:
<223> OTHER INFORMATION: chemically synthesized

<400> SEQUENCE: 1
gacgatcgtc                                                            10

<210> SEQ ID NO 2
<211> LENGTH: 18
<212> TYPE: DNA
<213> ORGANISM: Artificial Sequence
<220> FEATURE:
<223> OTHER INFORMATION: chemically synthesized

<400> SEQUENCE: 2
gggggacgat cgtcgggg                                                   18

<210> SEQ ID NO 3
<211> LENGTH: 20
<212> TYPE: DNA
<213> ORGANISM: Artificial Sequence
<220> FEATURE:
<223> OTHER INFORMATION: chemically synthesized

<400> SEQUENCE: 3
ggggggacga tcgtcggggg                                                 20

<210> SEQ ID NO 4
<211> LENGTH: 22
<212> TYPE: DNA
<213> ORGANISM: Artificial Sequence
<220> FEATURE:
<223> OTHER INFORMATION: chemically synthesized

<400> SEQUENCE: 4
gggggggacg atcgtcgggg gg                                              22
```

```
<210> SEQ ID NO 5
<211> LENGTH: 24
<212> TYPE: DNA
<213> ORGANISM: Artificial Sequence
<220> FEATURE:
<223> OTHER INFORMATION: chemically synthesized

<400> SEQUENCE: 5
ggggggggac gatcgtcggg gggg                                          24

<210> SEQ ID NO 6
<211> LENGTH: 26
<212> TYPE: DNA
<213> ORGANISM: Artificial Sequence
<220> FEATURE:
<223> OTHER INFORMATION: chemically synthesized

<400> SEQUENCE: 6
ggggggggga cgatcgtcgg gggggg                                        26

<210> SEQ ID NO 7
<211> LENGTH: 28
<212> TYPE: DNA
<213> ORGANISM: Artificial Sequence
<220> FEATURE:
<223> OTHER INFORMATION: chemically synthesized

<400> SEQUENCE: 7
gggggggggg acgatcgtcg gggggggg                                      28

<210> SEQ ID NO 8
<211> LENGTH: 30
<212> TYPE: DNA
<213> ORGANISM: Artificial Sequence
<220> FEATURE:
<223> OTHER INFORMATION: chemically synthesized

<400> SEQUENCE: 8
gggggggggg gacgatcgtc gggggggggg                                    30

<210> SEQ ID NO 9
<211> LENGTH: 32
<212> TYPE: DNA
<213> ORGANISM: Artificial Sequence
<220> FEATURE:
<223> OTHER INFORMATION: chemically synthesized

<400> SEQUENCE: 9
gggggggggg ggacgatcgt cgggggggggg gg                                32

<210> SEQ ID NO 10
<211> LENGTH: 132
<212> TYPE: PRT
<213> ORGANISM: bacteriophage Qb

<400> SEQUENCE: 10

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60
```

-continued

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
        130

<210> SEQ ID NO 11
<211> LENGTH: 329
<212> TYPE: PRT
<213> ORGANISM: bacteriophage Qb

<400> SEQUENCE: 11

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr Trp Thr Leu Leu Ile Ala Gly Gly Gly Ser Gly
    130                 135                 140

Ser Lys Pro Asp Pro Val Ile Pro Asp Pro Pro Ile Asp Pro Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
        195                 200                 205

Gly Asn Thr Lys Trp Arg Asp Trp Asp Ser Arg Leu Ser Tyr Thr Thr
    210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
        275                 280                 285

Ala Asp Gly Val Ile Val Gly Phe Trp Arg Asp Pro Ser Ser Gly Gly
    290                 295                 300

```
Ala Ile Pro Phe Asp Phe Thr Lys Phe Asp Lys Thr Lys Cys Pro Ile
305                 310                 315                 320

Gln Ala Val Ile Val Val Pro Arg Ala
            325
```

<210> SEQ ID NO 12
<211> LENGTH: 129
<212> TYPE: PRT
<213> ORGANISM: bacteriophage R17

<400> SEQUENCE: 12

```
Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Met Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr
```

<210> SEQ ID NO 13
<211> LENGTH: 130
<212> TYPE: PRT
<213> ORGANISM: bacteriophage fr

<400> SEQUENCE: 13

```
Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Asn Asn Arg Lys Tyr Thr Val Lys Val Glu
    50                  55                  60

Val Pro Lys Val Ala Thr Gln Val Gln Gly Gly Val Glu Leu Pro Val
65                  70                  75                  80

Ala Ala Trp Arg Ser Tyr Met Asn Met Glu Leu Thr Ile Pro Val Phe
                85                  90                  95

Ala Thr Asn Asp Asp Cys Ala Leu Ile Val Lys Ala Leu Gln Gly Thr
            100                 105                 110

Phe Lys Thr Gly Asn Pro Ile Ala Thr Ala Ile Ala Ala Asn Ser Gly
        115                 120                 125

Ile Tyr
    130
```

<210> SEQ ID NO 14
<211> LENGTH: 130
<212> TYPE: PRT
<213> ORGANISM: bacteriophage GA

<400> SEQUENCE: 14

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
            20                  25                  30

Leu Ser Asn Asn Ser Arg Ser Gln Ala Tyr Arg Val Thr Ala Ser Tyr
        35                  40                  45

Arg Ala Ser Gly Ala Asp Lys Arg Tyr Ala Ile Lys Leu Glu Val
    50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130

<210> SEQ ID NO 15
<211> LENGTH: 132
<212> TYPE: PRT
<213> ORGANISM: bacteriophage SP

<400> SEQUENCE: 15

Met Ala Lys Leu Asn Gln Val Thr Leu Ser Lys Ile Gly Lys Asn Gly
1               5                   10                  15

Asp Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Phe Lys
    50                  55                  60

Val Gln Ile Lys Leu Gln Asn Pro Thr Ala Cys Thr Arg Asp Ala Cys
65                  70                  75                  80

Asp Pro Ser Val Thr Arg Ser Ala Phe Ala Asp Val Thr Leu Ser Phe
                85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
    130

<210> SEQ ID NO 16
<211> LENGTH: 329
<212> TYPE: PRT
<213> ORGANISM: bacteriophage SP

<400> SEQUENCE: 16

Ala Lys Leu Asn Gln Val Thr Leu Ser Lys Ile Gly Lys Asn Gly Asp
1               5                   10                  15

Gln Thr Leu Thr Leu Thr Pro Arg Gly Val Asn Pro Thr Asn Gly Val
            20                  25                  30

Ala Ser Leu Ser Glu Ala Gly Ala Val Pro Ala Leu Glu Lys Arg Val

```
                35                  40                  45
Thr Val Ser Val Ala Gln Pro Ser Arg Asn Arg Lys Asn Phe Lys Val
        50                  55                  60
Gln Ile Lys Leu Gln Asn Pro Thr Ala Cys Thr Arg Asp Ala Cys Asp
 65                  70                  75                  80
Pro Ser Val Thr Arg Ser Ala Phe Ala Asp Val Thr Leu Ser Phe Thr
                85                  90                  95
Ser Tyr Ser Thr Asp Glu Glu Arg Ala Leu Ile Arg Thr Glu Leu Ala
                100                 105                 110
Ala Leu Leu Ala Asp Pro Leu Ile Val Asp Ala Ile Asp Asn Leu Asn
                115                 120                 125
Pro Ala Tyr Trp Ala Ala Leu Leu Val Ala Ser Ser Gly Gly Gly Asp
                130                 135                 140
Asn Pro Ser Asp Pro Asp Val Pro Val Val Pro Asp Val Lys Pro Pro
145                 150                 155                 160
Asp Gly Thr Gly Arg Tyr Lys Cys Pro Phe Ala Cys Tyr Arg Leu Gly
                165                 170                 175
Ser Ile Tyr Glu Val Gly Lys Glu Gly Ser Pro Asp Ile Tyr Glu Arg
                180                 185                 190
Gly Asp Glu Val Ser Val Thr Phe Asp Tyr Ala Leu Glu Asp Phe Leu
                195                 200                 205
Gly Asn Thr Asn Trp Arg Asn Trp Asp Gln Arg Leu Ser Asp Tyr Asp
                210                 215                 220
Ile Ala Asn Arg Arg Arg Cys Arg Gly Asn Gly Tyr Ile Asp Leu Asp
225                 230                 235                 240
Ala Thr Ala Met Gln Ser Asp Asp Phe Val Leu Ser Gly Arg Tyr Gly
                245                 250                 255
Val Arg Lys Val Lys Phe Pro Gly Ala Phe Gly Ser Ile Lys Tyr Leu
                260                 265                 270
Leu Asn Ile Gln Gly Asp Ala Trp Leu Asp Leu Ser Glu Val Thr Ala
                275                 280                 285
Tyr Arg Ser Tyr Gly Met Val Ile Gly Phe Trp Thr Asp Ser Lys Ser
                290                 295                 300
Pro Gln Leu Pro Thr Asp Phe Thr Gln Phe Asn Ser Ala Asn Cys Pro
305                 310                 315                 320
Val Gln Thr Val Ile Ile Pro Ser
                325

<210> SEQ ID NO 17
<211> LENGTH: 130
<212> TYPE: PRT
<213> ORGANISM: bacteriophage MS2

<400> SEQUENCE: 17

Met Ala Ser Asn Phe Thr Gln Phe Val Leu Val Asp Asn Gly Gly Thr
 1               5                  10                  15
Gly Asp Val Thr Val Ala Pro Ser Asn Phe Ala Asn Gly Val Ala Glu
                20                  25                  30
Trp Ile Ser Ser Asn Ser Arg Ser Gln Ala Tyr Lys Val Thr Cys Ser
                35                  40                  45
Val Arg Gln Ser Ser Ala Gln Asn Arg Lys Tyr Thr Ile Lys Val Glu
                50                  55                  60
Val Pro Lys Val Ala Thr Gln Thr Val Gly Gly Val Glu Leu Pro Val
 65                  70                  75                  80
Ala Ala Trp Arg Ser Tyr Leu Asn Met Glu Leu Thr Ile Pro Ile Phe
```

```
                    85                  90                  95
Ala Thr Asn Ser Asp Cys Glu Leu Ile Val Lys Ala Met Gln Gly Leu
                100                 105                 110

Leu Lys Asp Gly Asn Pro Ile Pro Ser Ala Ile Ala Ala Asn Ser Gly
        115                 120                 125

Ile Tyr
    130

<210> SEQ ID NO 18
<211> LENGTH: 133
<212> TYPE: PRT
<213> ORGANISM: bacteriophage M11

<400> SEQUENCE: 18

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
                100                 105                 110

Leu Gln Ala Leu Leu Ala Asp Pro Met Leu Val Asn Ala Ile Asp Asn
        115                 120                 125

Leu Asn Pro Ala Tyr
    130

<210> SEQ ID NO 19
<211> LENGTH: 133
<212> TYPE: PRT
<213> ORGANISM: bacteriophage MX1

<400> SEQUENCE: 19

Met Ala Lys Leu Gln Ala Ile Thr Leu Ser Gly Ile Gly Lys Asn Gly
1               5                   10                  15

Asp Val Thr Leu Asn Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ala Asp Val Thr Phe Ser
                85                  90                  95

Phe Thr Gln Tyr Ser Thr Asp Glu Glu Arg Ala Leu Val Arg Thr Glu
                100                 105                 110

Leu Lys Ala Leu Leu Ala Asp Pro Met Leu Ile Asp Ala Ile Asp Asn
        115                 120                 125

Leu Asn Pro Ala Tyr
    130
```

<210> SEQ ID NO 20
<211> LENGTH: 330
<212> TYPE: PRT
<213> ORGANISM: bacteriophage NL95

<400> SEQUENCE: 20

Met Ala Lys Leu Asn Lys Val Thr Leu Thr Gly Ile Gly Lys Ala Gly
1               5                   10                  15

Asn Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Tyr Lys
    50                  55                  60

Val Gln Ile Lys Leu Gln Asn Pro Thr Ala Cys Thr Lys Asp Ala Cys
65                  70                  75                  80

Asp Pro Ser Val Thr Arg Ser Gly Ser Arg Asp Val Thr Leu Ser Phe
                85                  90                  95

Thr Ser Tyr Ser Thr Glu Arg Glu Arg Ala Leu Ile Arg Thr Glu Leu
            100                 105                 110

Ala Ala Leu Leu Lys Asp Asp Leu Ile Val Asp Ala Ile Asp Asn Leu
        115                 120                 125

Asn Pro Ala Tyr Trp Ala Ala Leu Leu Ala Ala Ser Pro Gly Gly Gly
    130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
                165                 170                 175

Glu Leu Ile Thr Glu Ala Lys Asp Gly Ala Cys Ala Leu Tyr Ala Cys
            180                 185                 190

Gly Ser Glu Ala Leu Val Glu Phe Glu Tyr Ala Leu Glu Asp Phe Leu
        195                 200                 205

Gly Asn Glu Phe Trp Arg Asn Trp Asp Gly Arg Leu Ser Lys Tyr Asp
    210                 215                 220

Ile Glu Thr His Arg Arg Cys Arg Gly Asn Gly Tyr Val Asp Leu Asp
225                 230                 235                 240

Ala Ser Val Met Gln Ser Asp Glu Tyr Val Leu Ser Gly Ala Tyr Asp
                245                 250                 255

Val Val Lys Met Gln Pro Pro Gly Thr Phe Asp Ser Pro Arg Tyr Tyr
            260                 265                 270

Leu His Leu Met Asp Gly Ile Tyr Val Asp Leu Ala Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Arg Phe Asn Arg His Asn Cys Pro
305                 310                 315                 320

Val Gln Thr Val Ile Val Ile Pro Ser Leu
                325                 330

<210> SEQ ID NO 21
<211> LENGTH: 129
<212> TYPE: PRT
<213> ORGANISM: bacteriophage f2

<400> SEQUENCE: 21

```
Ala Ser Asn Phe Thr Gln Phe Val Leu Val Asn Asp Gly Gly Thr Gly
 1               5                  10                 15

Asn Val Thr Val Ala Pro Ser Asn Phe Ala Asn Gly Val Ala Glu Trp
                20                  25                 30

Ile Ser Ser Asn Ser Arg Ser Gln Ala Tyr Lys Val Thr Cys Ser Val
            35                  40                  45

Arg Gln Ser Ser Ala Gln Asn Arg Lys Tyr Thr Ile Lys Val Glu Val
        50                  55                  60

Pro Lys Val Ala Thr Gln Thr Val Gly Gly Val Glu Leu Pro Val Ala
 65                 70                  75                  80

Ala Trp Arg Ser Tyr Leu Asn Leu Glu Leu Thr Ile Pro Ile Phe Ala
                85                  90                  95

Thr Asn Ser Asp Cys Glu Leu Ile Val Lys Ala Met Gln Gly Leu Leu
                100                 105                 110

Lys Asp Gly Asn Pro Ile Pro Ser Ala Ile Ala Ala Asn Ser Gly Ile
            115                 120                 125

Tyr

<210> SEQ ID NO 22
<211> LENGTH: 128
<212> TYPE: PRT
<213> ORGANISM: bacteriophage PP7

<400> SEQUENCE: 22

Met Ser Lys Thr Ile Val Leu Ser Val Gly Glu Ala Thr Arg Thr Leu
 1               5                  10                 15

Thr Glu Ile Gln Ser Thr Ala Asp Arg Gln Ile Phe Glu Glu Lys Val
                20                  25                 30

Gly Pro Leu Val Gly Arg Leu Arg Leu Thr Ala Ser Leu Arg Gln Asn
            35                  40                  45

Gly Ala Lys Thr Ala Tyr Arg Val Asn Leu Lys Leu Asp Gln Ala Asp
        50                  55                  60

Val Val Asp Cys Ser Thr Ser Val Cys Gly Glu Leu Pro Lys Val Arg
 65                 70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
                100                 105                 110

Thr Ser Gln Val Glu Asp Leu Val Val Asn Leu Val Pro Leu Gly Arg
            115                 120                 125

<210> SEQ ID NO 23
<211> LENGTH: 131
<212> TYPE: PRT
<213> ORGANISM: bacteriophage AP205

<400> SEQUENCE: 23

Met Ala Asn Lys Pro Met Gln Pro Ile Thr Ser Thr Ala Asn Lys Ile
 1               5                  10                 15

Val Trp Ser Asp Pro Thr Arg Leu Ser Thr Thr Phe Ser Ala Ser Leu
                20                  25                 30

Leu Arg Gln Arg Val Lys Val Gly Ile Ala Glu Leu Asn Asn Val Ser
            35                  40                  45

Gly Gln Tyr Val Ser Val Tyr Lys Arg Pro Ala Pro Lys Pro Glu Gly
        50                  55                  60

Cys Ala Asp Ala Cys Val Ile Met Pro Asn Glu Asn Gln Ser Ile Arg
 65                 70                  75                  80
```

```
Thr Val Ile Ser Gly Ser Ala Glu Asn Leu Ala Thr Leu Lys Ala Glu
            85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
            115                 120                 125

Thr Thr Ala
    130
```